(12) United States Patent
Lim et al.

(10) Patent No.: US 10,576,006 B2
(45) Date of Patent: Mar. 3, 2020

(54) SURGICAL FRAME HAVING TRANSLATING LOWER BEAM AND METHOD FOR USE THEREOF

(71) Applicant: Warsaw Orthopedic, Inc, Warsaw (IN)

(72) Inventors: Roy K Lim, Germantown, TN (US); Matthew M Morrison, Cordova, TN (US); Thomas V. McGahan, Germantown, TN (US); Richard A. Hynes, Melbourne Beach, FL (US); Jason Waldo, Lynnfield, MA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 334 days.

(21) Appl. No.: 15/639,080

(22) Filed: Jun. 30, 2017

(65) Prior Publication Data
US 2019/0000707 A1 Jan. 3, 2019

(51) Int. Cl.
| | | |
|---|---|---|
| *A61G 13/12* | (2006.01) | |
| *A61G 13/04* | (2006.01) | |
| *A61B 6/04* | (2006.01) | |
| *A61G 13/10* | (2006.01) | |

(52) U.S. Cl.
CPC .............. *A61G 13/128* (2013.01); *A61B 6/04* (2013.01); *A61G 13/04* (2013.01); *A61G 13/105* (2013.01)

(58) Field of Classification Search
CPC ...... A61G 13/04; A61G 13/08; A61G 13/128; A61G 13/105; A61G 13/1235; A61G 13/1245; A61G 13/1295; A61G 13/121; A61G 13/122; A61G 2200/322; A61G 2200/325; A61B 6/04
See application file for complete search history.

(56) References Cited

U.S. PATENT DOCUMENTS

| | | | |
|---|---|---|---|
| 2,691,979 | A | 10/1954 | Watson |
| 3,227,440 | A | 1/1966 | Scott |
| 3,306,287 | A | 2/1967 | Arp |
| 3,828,377 | A | 8/1974 | Fary, Sr. |
| 4,029,089 | A | 6/1977 | Mulhlland |
| 4,705,026 | A | 11/1987 | Chaussy |
| 4,866,796 | A | 9/1989 | Robinson |
| 4,872,656 | A | 10/1989 | Brendgord |
| 4,901,384 | A | 2/1990 | Eary |
| 5,009,407 | A | 4/1991 | Watanabe |

(Continued)

FOREIGN PATENT DOCUMENTS

| | | |
|---|---|---|
| WO | 2007058673 A1 | 5/2007 |
| WO | 2017031225 A1 | 2/2017 |

OTHER PUBLICATIONS

International Search Report dated Nov. 21, 2016 from International Application No. PCT/US2016/047394.

*Primary Examiner* — Nicholas F Polito
*Assistant Examiner* — Alexis Felix Lopez

(57) ABSTRACT

A surgical frame and method for use thereof is provided. The surgical frame is capable of reconfiguration before, during, or after surgery. The surgical includes a translating beam that is moveable between at least a first lateral position and a second lateral position. The translating beam is used to join a first support portion and a second support portion of the surgical frame to one another, and movement of the translating beam affords access to a patient receiving area.

20 Claims, 30 Drawing Sheets

(56) References Cited

U.S. PATENT DOCUMENTS

| | | | |
|---|---|---|---|
| 5,088,706 A * | 2/1992 | Jackson | A61G 13/00 5/608 |
| 5,103,511 A | 4/1992 | Sequin | |
| 5,131,106 A | 7/1992 | Jackson | |
| 5,390,383 A | 2/1995 | Carn | |
| 5,410,769 A | 5/1995 | Waterman | |
| 5,444,882 A | 8/1995 | Andrews | |
| 5,613,254 A | 3/1997 | Clayman | |
| 5,642,302 A | 6/1997 | Dumont | |
| 5,860,899 A | 1/1999 | Rassman | |
| 5,991,651 A | 11/1999 | LaBarbera | |
| 6,003,176 A | 12/1999 | Wasley | |
| 6,076,525 A | 6/2000 | Hoffman | |
| 6,154,901 A | 12/2000 | Carr | |
| 6,260,220 B1 | 7/2001 | Lamb | |
| 6,295,671 B1 | 10/2001 | Reesby et al. | |
| 6,311,349 B1 | 11/2001 | Kazakia | |
| 6,367,104 B1 | 4/2002 | Falbo, Sr. et al. | |
| 6,378,149 B1 | 4/2002 | Sanders et al. | |
| 6,516,483 B1 | 2/2003 | VanSteenburg | |
| 6,615,430 B2 | 9/2003 | Heimbrock | |
| 6,681,423 B2 | 1/2004 | Zachrisson | |
| 6,701,554 B2 | 3/2004 | Heimbrock | |
| 6,701,558 B2 | 3/2004 | VanSteenburg | |
| 6,739,006 B2 | 5/2004 | Borders et al. | |
| 6,941,951 B2 | 9/2005 | Hubert et al. | |
| 6,966,081 B1 | 11/2005 | Sharps | |
| 7,100,225 B1 | 9/2006 | Bailey | |
| 7,189,214 B1 | 3/2007 | Saunders | |
| 7,234,180 B2 | 6/2007 | Horton et al. | |
| 7,290,302 B2 | 11/2007 | Sharps | |
| 7,426,930 B1 | 9/2008 | Bailey | |
| 7,484,253 B1 | 2/2009 | Coppens | |
| 7,496,980 B2 | 3/2009 | Sharps | |
| 7,600,281 B2 | 10/2009 | Skripps | |
| 7,669,262 B2 | 3/2010 | Skripps | |
| 7,739,762 B2 | 6/2010 | Lamb et al. | |
| 7,882,583 B2 | 2/2011 | Skripps | |
| 8,118,029 B2 | 2/2012 | Gneiting et al. | |
| 8,234,730 B2 | 10/2012 | Copeland et al. | |
| 8,286,283 B2 | 10/2012 | Copeland et al. | |
| 8,286,637 B2 | 10/2012 | Kaska | |
| 8,413,660 B2 | 4/2013 | Weinstein et al. | |
| 8,439,948 B1 | 5/2013 | King | |
| 8,443,473 B2 | 5/2013 | Maxwell | |
| 8,584,281 B2 | 11/2013 | Diel et al. | |
| 8,635,725 B2 | 1/2014 | Tannoury et al. | |
| 9,072,646 B2 | 7/2015 | Skripps et al. | |
| 9,265,680 B2 | 2/2016 | Sharps | |
| 9,358,170 B2 | 6/2016 | Jackson | |
| 9,414,982 B2 | 8/2016 | Jackson | |
| 9,498,397 B2 | 11/2016 | Hight et al. | |
| 9,522,078 B2 | 12/2016 | Pizzini | |
| 9,554,959 B2 | 1/2017 | Carn | |
| 9,655,793 B2 | 5/2017 | Hertz | |
| 9,700,476 B2 | 7/2017 | Hoel et al. | |
| 9,713,562 B2 | 7/2017 | Perlman et al. | |
| 9,744,089 B2 | 8/2017 | Jackson | |
| 9,993,380 B2 | 6/2018 | Jackson | |
| 2004/0133983 A1 | 7/2004 | Newkirk | |
| 2005/0181917 A1 | 8/2005 | Dayal | |
| 2006/0123546 A1 | 6/2006 | Horton | |
| 2006/0162084 A1 | 7/2006 | Mezue | |
| 2008/0134434 A1 | 6/2008 | Celauro | |
| 2009/0139030 A1 | 6/2009 | Yang | |
| 2010/0037397 A1 | 2/2010 | Wood | |
| 2010/0192300 A1 | 8/2010 | Tannoury | |
| 2010/0293713 A1 * | 11/2010 | Sharps | A61G 7/001 5/86.1 |
| 2011/0030702 A1 | 2/2011 | Czajka, Jr. | |
| 2012/0144589 A1 | 6/2012 | Skripps et al. | |
| 2012/0144689 A1 | 6/2012 | Skripps et al. | |
| 2013/0111666 A1 | 5/2013 | Jackson | |
| 2013/0247921 A1 | 9/2013 | Dye | |
| 2013/0283526 A1 | 10/2013 | Gagliardi | |
| 2013/0307298 A1 | 11/2013 | Meiki | |
| 2014/0068861 A1 | 3/2014 | Jackson | |
| 2014/0109316 A1 | 4/2014 | Jackson et al. | |
| 2014/0137327 A1 | 5/2014 | Tannoury et al. | |
| 2015/0044956 A1 | 2/2015 | Hacker | |
| 2016/0047394 A1 | 2/2016 | Lim et al. | |
| 2016/0081582 A1 | 3/2016 | Rapoport | |
| 2016/0089287 A1 | 3/2016 | Buerstner | |
| 2016/0193099 A1 | 7/2016 | Drake | |
| 2017/0049651 A1 | 2/2017 | Lim et al. | |
| 2017/0049653 A1 | 2/2017 | Lim et al. | |
| 2017/0079864 A1 | 3/2017 | Riley | |
| 2017/0135891 A1 | 5/2017 | Kettner et al. | |
| 2017/0341232 A1 | 11/2017 | Perplies et al. | |
| 2018/0116891 A1 | 5/2018 | Beale et al. | |
| 2018/0193104 A1 | 7/2018 | Beale et al. | |
| 2018/0363596 A1 | 12/2018 | Lim et al. | |
| 2019/0000702 A1 | 1/2019 | Lim et al. | |
| 2019/0000707 A1 | 1/2019 | Lim et al. | |
| 2019/0046381 A1 | 2/2019 | Lim et al. | |
| 2019/0046383 A1 | 2/2019 | Lim et al. | |

* cited by examiner

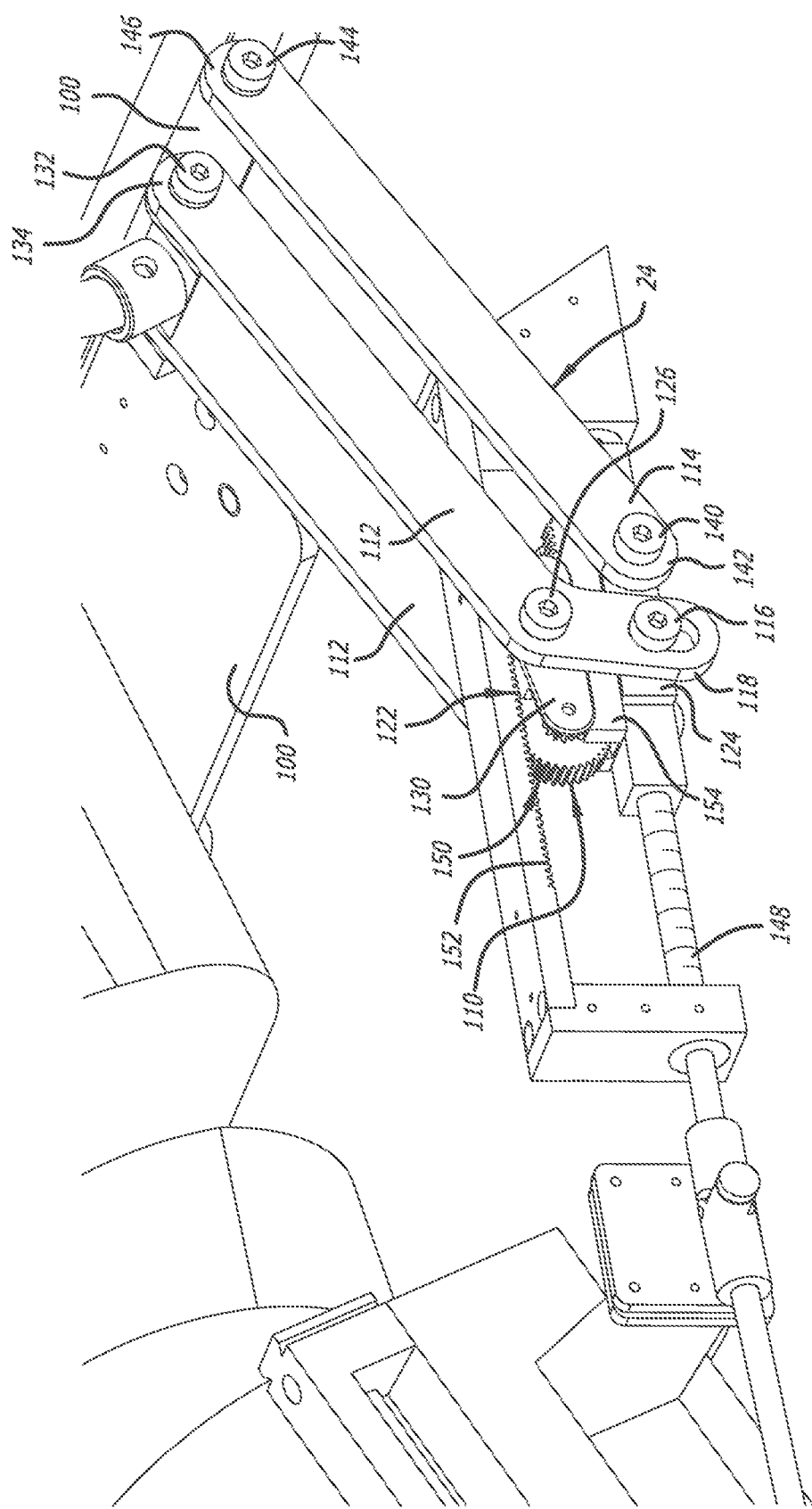

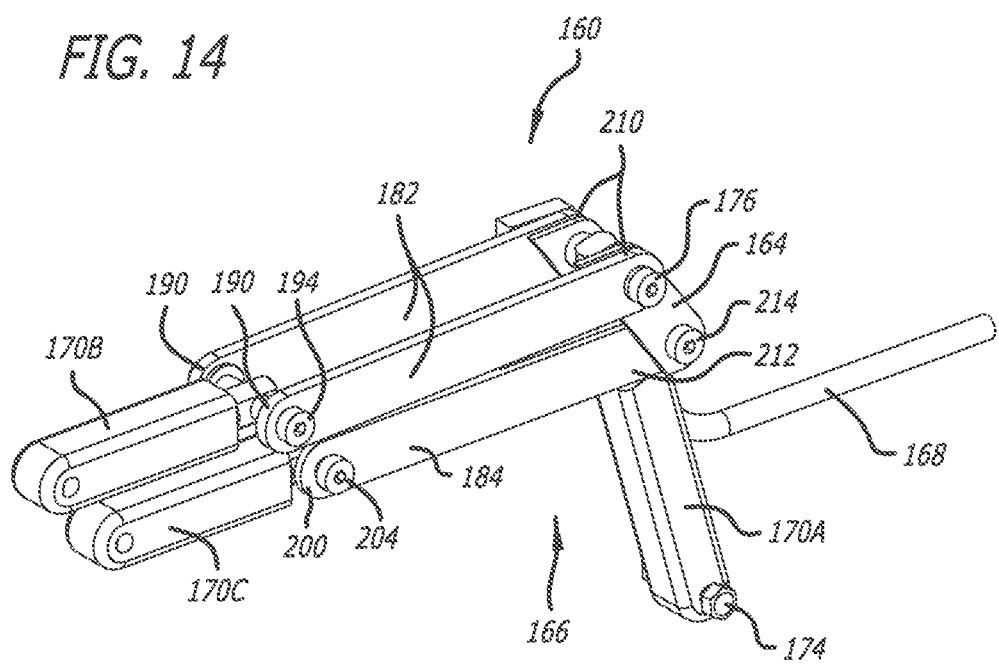

SURGICAL FRAME HAVING TRANSLATING LOWER BEAM AND METHOD FOR USE THEREOF

BACKGROUND OF THE INVENTION

Field of the Invention

The present invention relates to a surgical frame and a method for use thereof incorporating a translating lower beam. More particularly, the present invention relates to a surgical frame and a method for use thereof, where the surgical frame includes a translating lower beam that is moveable with respect to the remainder of the surgical frame. More specifically, the present invention relates to a surgical frame and a method for use thereof, where the surgical frame includes a translating lower beam that can be positioned and repositioned to afford greater access to a patient receiving area to facilitate transfer to and from the surgical frame, and to afford greater access to a patient by a surgeon and/or a surgical assistant.

Description of the Prior Art

Typically, surgical frames used to support patients thereon include cross members extending between opposite ends thereof. A typical cross member extends horizontally from one end to the other end of the surgical frame, and the typical cross member serves to tie both ends of the surgical frame to one another. A typical cross member is fixed in position, and is located adjacent to the ground on which the surgical frame is positioned to lower the center of gravity of the surgical table. However, the fixed position and location of a typical cross member can create interference. For example, the fixed position and location of a typical cross member can interfere with transfer of a patient from and to a surgical table/gurney. Furthermore, the fixed position and location of a typical cross member can interfere with access to a patient by a surgeon and/or a surgical assistant. As such, there is a need for a surgical frame and a method for use thereof, where the surgical frame has a translating lower beam that can be positioned and repositioned to afford greater access to a patient receiving area to facilitate transfer to and from the surgical frame, and to afford greater access to a patient by a surgeon and/or a surgical assistant.

SUMMARY OF THE INVENTION

The present invention in one preferred embodiment contemplates a method of reconfiguring a surgical frame before, during, or after surgery, the method including spacing a main beam of the surgical frame and a patient positioned on the main beam from the ground with a first support portion and a second support portion; rotating the main beam and the patient positioned thereon from a prone position to one of a first lateral position and a second lateral position; and moving a translating beam under the main beam and the patient positioned thereon, the translating beam being moveable between a first position at or adjacent a first lateral side of the surgical frame and a second position at or adjacent a second lateral side of the surgical frame, and the translating beam joining portions of the surgical frame together between the first and second support portions.

The present invention in another preferred embodiment contemplates a method of reconfiguring a surgical frame before, during, or after surgery, the method including spacing a main beam of the surgical frame from the ground with a first support portion and a second support portion; supporting a patient by the main beam of the surgical frame; rotating the main beam and the patient positioned thereon from a prone position to one of a first lateral position and a second lateral position; and moving a translating beam under the main beam and the patient positioned thereon, the translating beam being moveable between a first position at or adjacent a first lateral side of the surgical frame and a second position at or adjacent a second lateral side of the surgical frame, and the translating beam joining portions of the surgical frame together between the first and second support portions.

The present invention in yet another preferred embodiment contemplates a method of reconfiguring a surgical frame before, during, or after surgery, the method including providing the surgical frame including a support platform, a first support portion, a second support portion, and a main beam spaced from the ground by the support platform, the first support portion, and the second support portion, the support platform including a translating beam moveable between a first position at or adjacent a first lateral side of the surgical frame and a second position at or adjacent a second lateral side of the surgical frame, the main beam being configured to receive a patient thereon, the main beam and the patient received thereon being rotatable relative to the support platform, the first support portion, and the second support portion; supporting the patient by the main beam of the surgical frame; rotating the patient to a prone position, and moving the translating beam to a position underneath the patient supported in the prone position; and rotating the patient to one of a first lateral position and a second lateral position, and moving the translating beam to a position underneath the patient supported in the one of the first lateral position and the second lateral position.

These and other objects of the present invention will be apparent from review of the following specification and the accompanying drawings.

BRIEF DESCRIPTION OF THE DRAWINGS

FIG. 12 is an enlarged top perspective view of the componentry of the torso-lift support in the lifted position;

FIG. 14 is a perspective view of a chest support lift mechanism of the torso-lift support of FIGS. 13A-13C with actuators thereof retracted;

DETAILED DESCRIPTION OF THE PREFERRED EMBODIMENT

Figure 1:
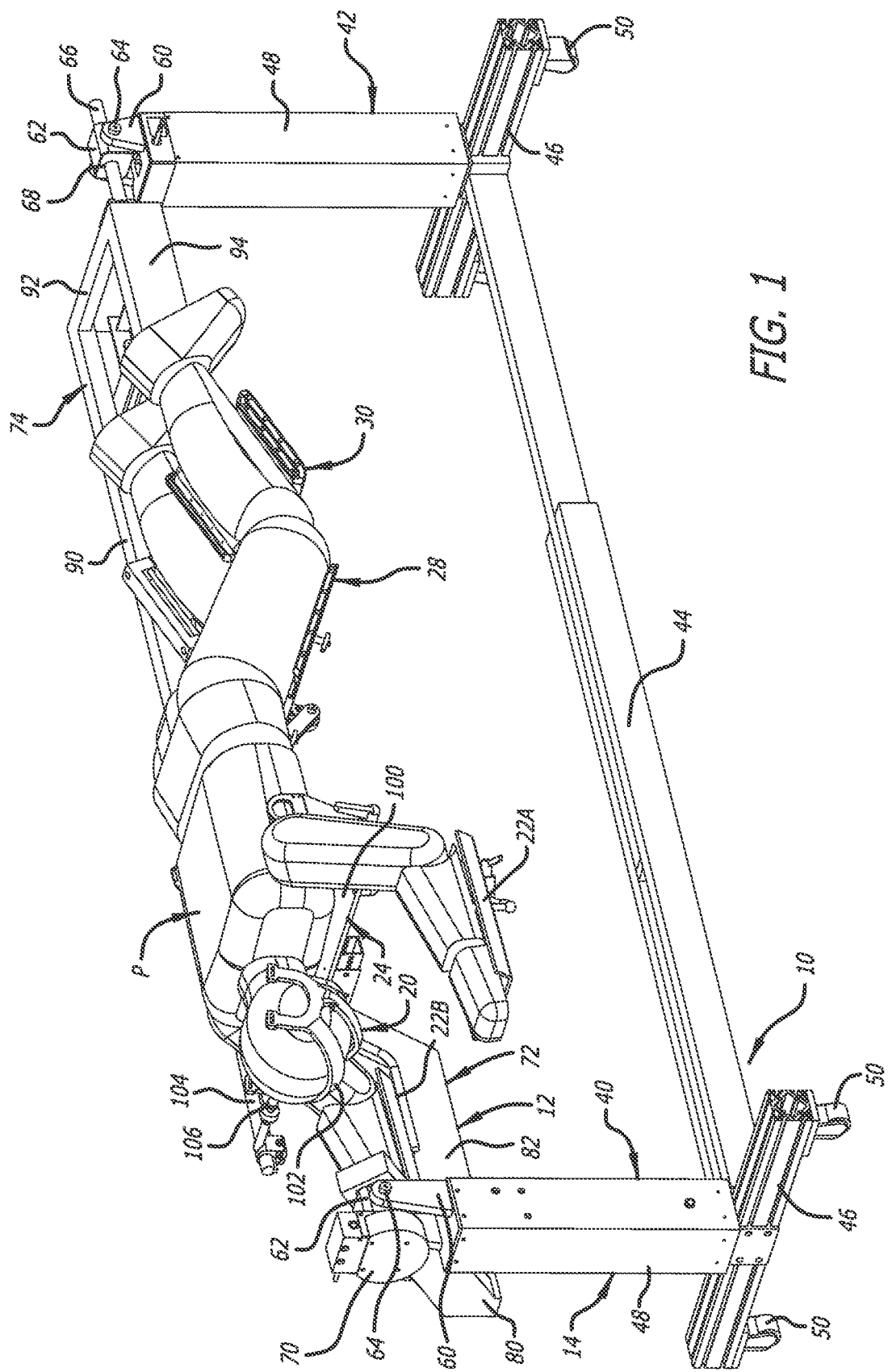
FIG. 1 is a top perspective view of a prior art surgical frame with a patient positioned thereon in a prone position.
Figure 2:
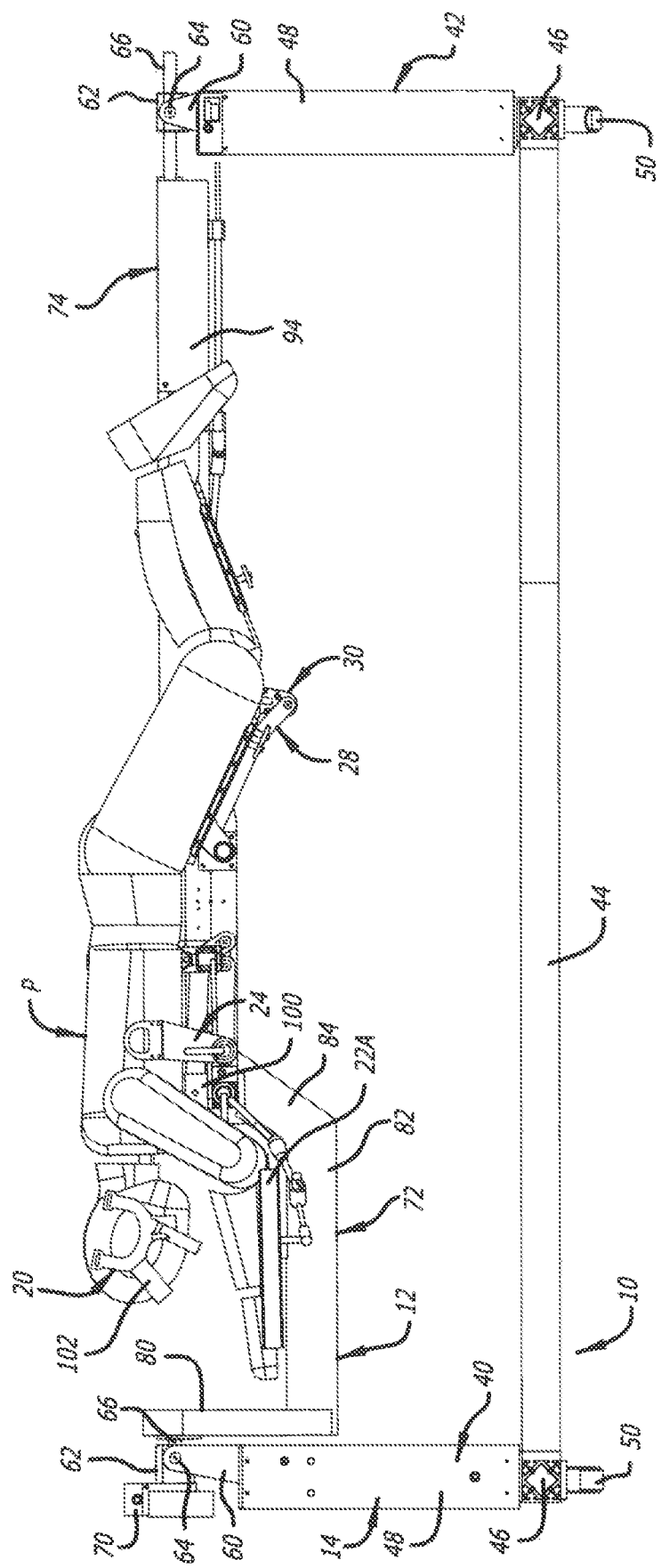
FIG. 2 is a side elevational view of the surgical frame of FIG. 1 with the patient positioned thereon in a prone position.
Figure 3:
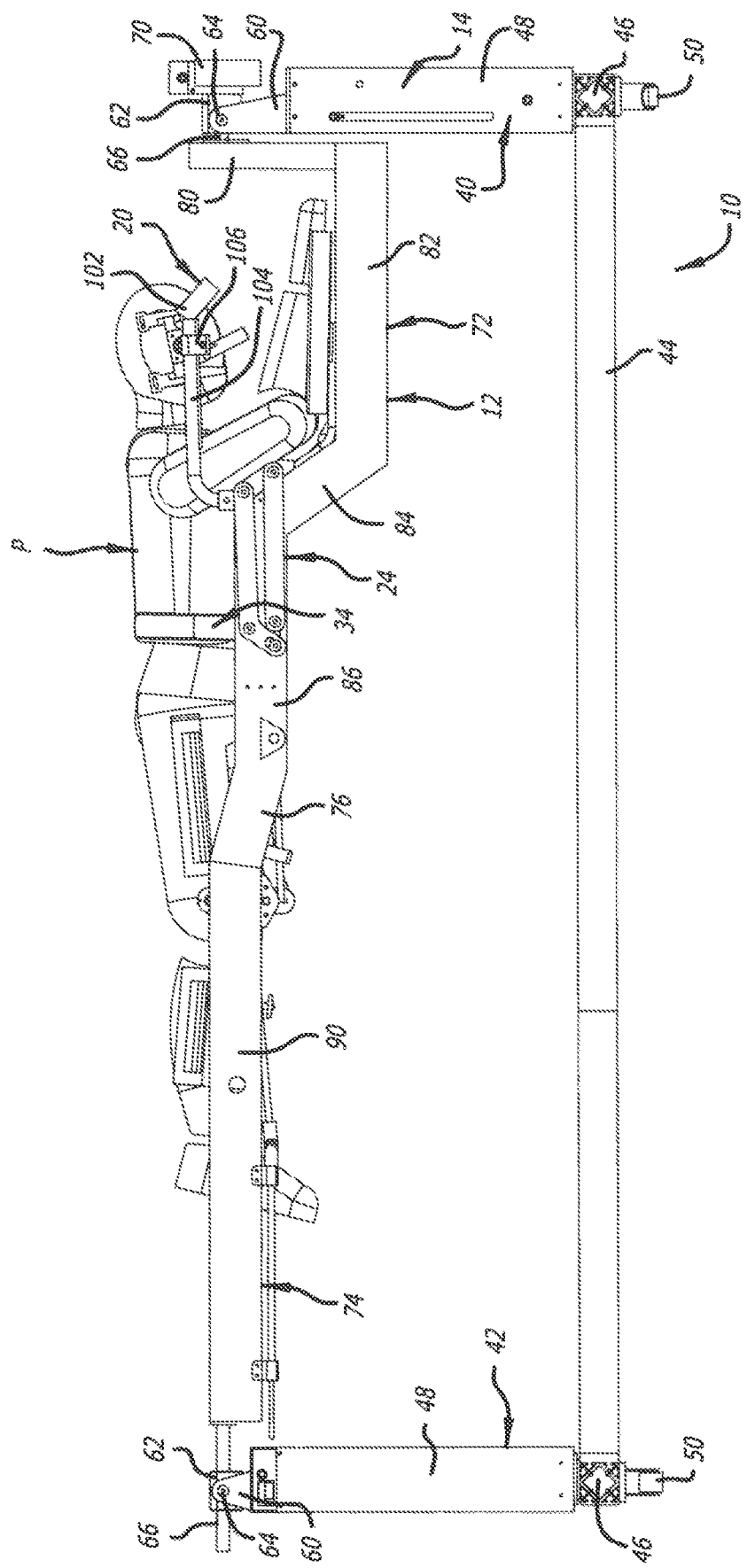
FIG. 3 is another side elevational view of the surgical frame of FIG. 1 with the patient positioned thereon in a prone position.

FIGS. 1-26 depict a prior art embodiment and components of a surgical support frame generally indicated by the numeral 10. FIGS. 1-26 were previously described in U.S. Ser. No. 15/239,256, which is hereby incorporated by reference herein in its entirety. As discussed below, the surgical frame 10 serves as an exoskeleton to support the body of the patient P as the patient's body is manipulated thereby, and, in doing so, serves to support the patient P such that the patient's spine does not experience unnecessary torsion.

The surgical frame 10 is configured to provide a relatively minimal amount of structure adjacent the patient's spine to facilitate access thereto and to improve the quality of imaging available before and during surgery. Thus, the surgeon's workspace and imaging access are thereby increased. Furthermore, radio-lucent or low magnetic susceptibility materials can be used in constructing the structural components adjacent the patient's spine in order to further enhance imaging quality.

The surgical frame 10 has a longitudinal axis and a length therealong. As depicted in FIGS. 1-5, for example, the surgical frame 10 includes an offset structural main beam 12 and a support structure 14. The offset main beam 12 is spaced from the ground by the support structure 14. As discussed below, the offset main beam 12 is used in supporting the patient P on the surgical frame 10 and various support components of the surgical frame 10 that directly contact the patient P (such as a head support 20, arm supports 22A and 22B, torso-lift supports 24 and 160, a sagittal adjustment assembly 28 including a pelvic-tilt mechanism 30 and a leg adjustment mechanism 32, and a coronal adjustment assembly 34). As discussed below, an operator such as a surgeon can control actuation of the various support components to manipulate the position of the patient's body. Soft straps (not shown) are used with these various support components to secure the patient P to the frame and to enable either manipulation or fixation of the patient P. Reusable soft pads can be used on the load-bearing areas of the various support components.

Figure 4:
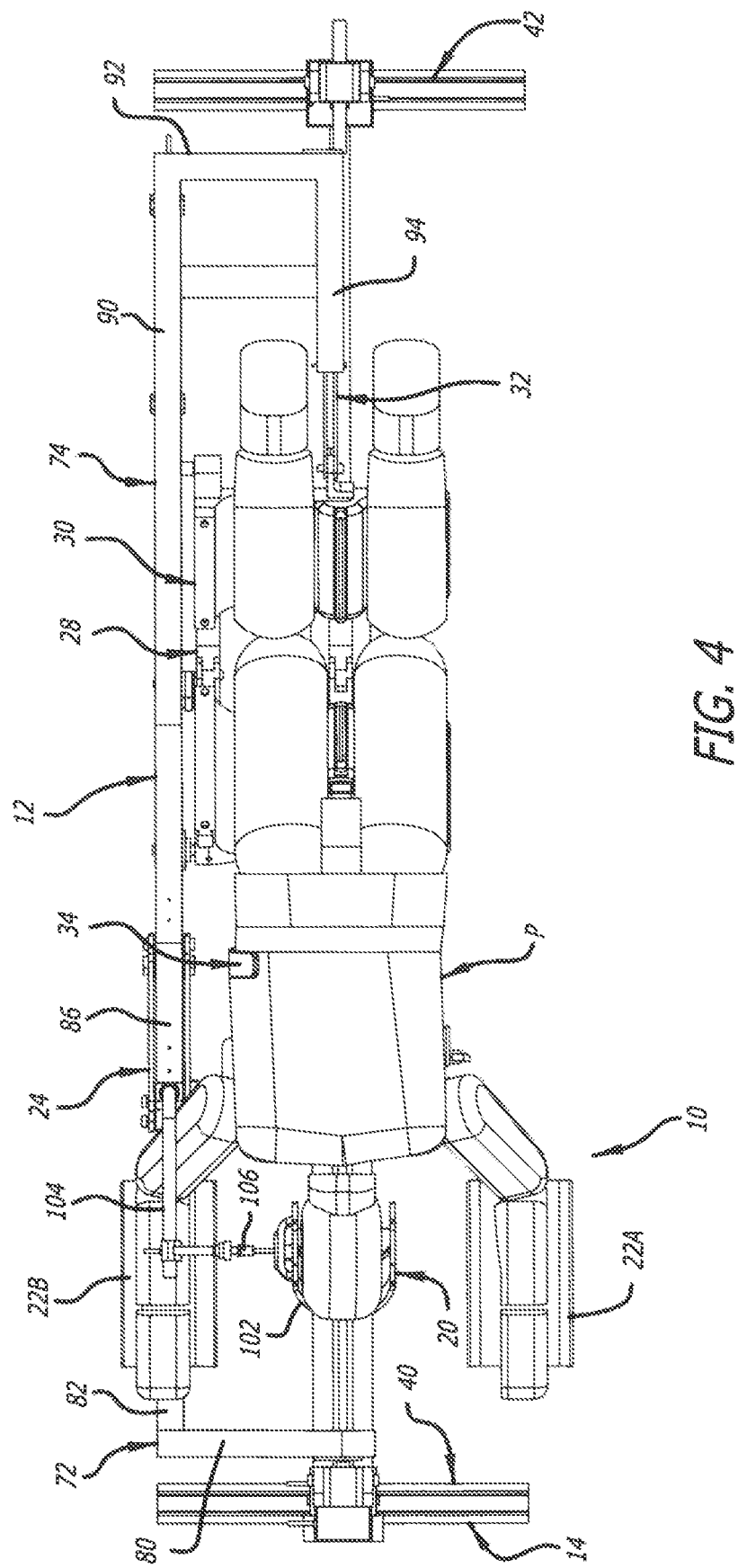
FIG. 4 is a top plan view of the surgical frame of FIG. 1 with the patient positioned thereon in a prone position.
Figure 5:
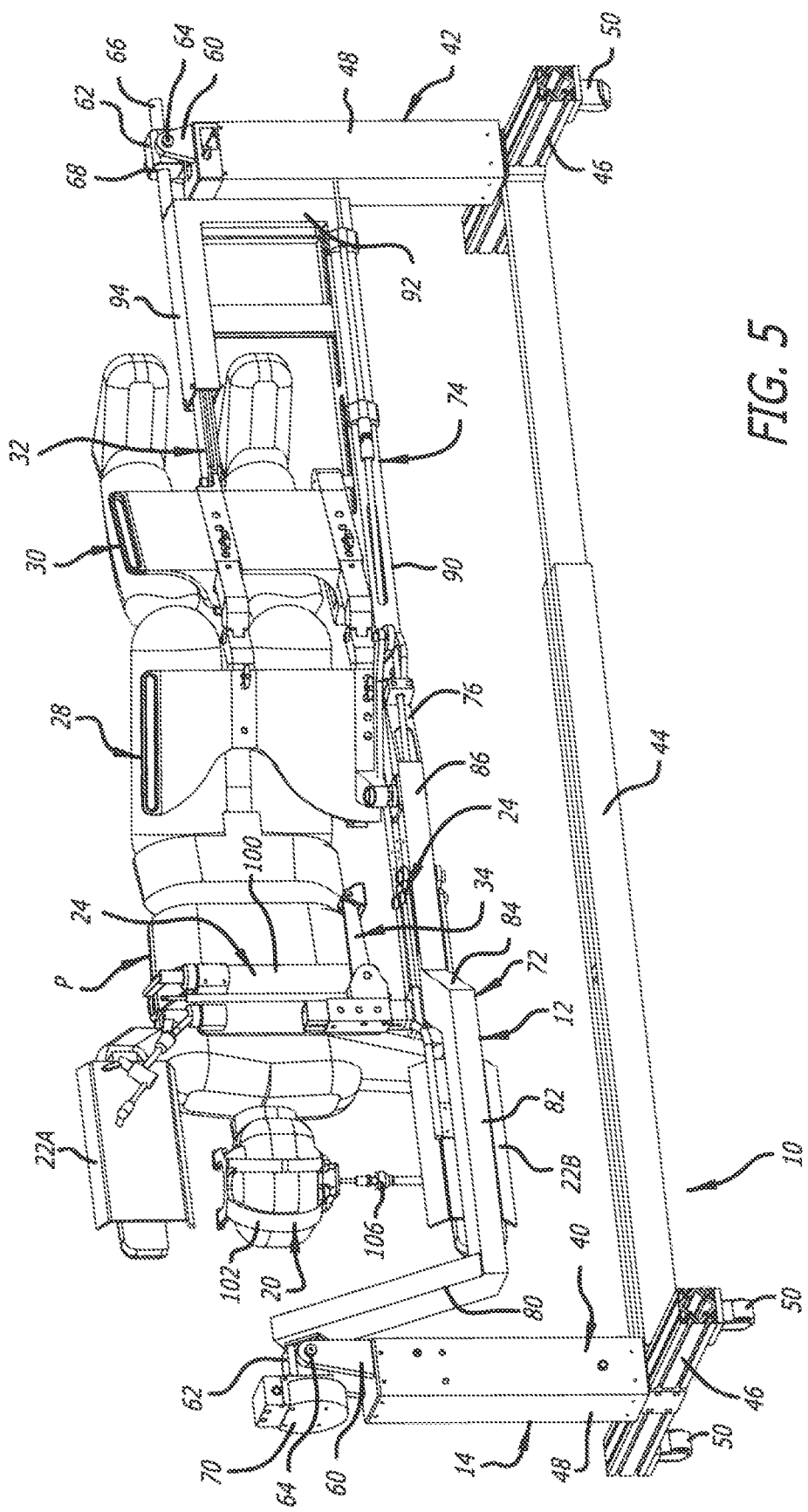
FIG. 5 is a top perspective view of the surgical frame of FIG. 1 with the patient positioned thereon in a lateral position.

The offset main beam 12 is used to facilitate rotation of the patient P. The offset main beam 12 can be rotated a full 360° before and during surgery to facilitate various positions of the patient P to afford various surgical pathways to the patient's spine depending on the surgery to be performed. For example, the offset main beam 12 can be positioned to place the patient P in a prone position (e.g., FIGS. 1-4), a lateral position (e.g., FIG. 5), and in a position 45° between the prone and lateral positions. Furthermore, the offset main beam 12 can be rotated to afford anterior, posterior, lateral, anterolateral, and posterolateral pathways to the spine. As such, the patient's body can be flipped numerous times before and during surgery without compromising sterility or safety. The various support components of the surgical frame 10 are strategically placed to further manipulate the patient's body into position before and during surgery. Such intraoperative manipulation and positioning of the patient P affords a surgeon significant access to the patient's body. To illustrate, when the offset main beam 12 is rotated to position the patient P in a lateral position, as depicted in FIG. 5, the head support 20, the arm supports 22A and 22B, the torso-lift support 24, the sagittal adjustment assembly 28, and/or the coronal adjustment assembly 34 can be articulated such that the surgical frame 10 is OLIF-capable or DLIF-capable.

As depicted in FIG. 1, for example, the support structure 14 includes a first support portion 40 and a second support portion 42 interconnected by a cross member 44. Each of the first and second support portions 40 and 42 include a horizontal portion 46 and a vertical support post 48. The horizontal portions 46 are connected to the cross member 44, and casters 50 can be attached to the horizontal portions 46 to facilitate movement of the surgical frame 10.

The vertical support posts 48 can be adjustable to facilitate expansion and contraction of the heights thereof. Expansion and contraction of the vertical support posts 48 facilitates raising and lowering, respectively, of the offset main beam 12. As such, the vertical support posts 48 can be adjusted to have equal or different heights. For example, the vertical support posts 48 can be adjusted such that the vertical support post 48 of the second support portion 42 is raised 12 inches higher than the vertical support post 48 of the first support portion 40 to place the patient P in a reverse Trendelenburg position.

Furthermore, cross member 44 can be adjustable to facilitate expansion and contraction of the length thereof. Expansion and contraction of the cross member 44 facilitates lengthening and shortening, respectively, of the distance between the first and second support portions 40 and 42.

The vertical support post 48 of the first and second support portions 40 and 42 have heights at least affording rotation of the offset main beam 12 and the patient P positioned thereon. Each of the vertical support posts 48 include a clevis 60, a support block 62 positioned in the clevis 60, and a pin 64 pinning the clevis 60 to the support block 62. The support blocks 62 are capable of pivotal movement relative to the devises 60 to accommodate different heights of the vertical support posts 48. Furthermore, axles 66 extending outwardly from the offset main beam 12 are received in apertures 68 formed the support blocks 62. The axles 66 define an axis of rotation of the offset main beam 12, and the interaction of the axles 66 with the support blocks 62 facilitate rotation of the offset main beam 12.

Furthermore, a servomotor 70 can be interconnected with the axle 66 received in the support block 62 of the first support portion 40. The servomotor 70 can be computer controlled and/or operated by the operator of the surgical frame 10 to facilitate controlled rotation of the offset main beam 12. Thus, by controlling actuation of the servomotor 70, the offset main beam 12 and the patient P supported thereon can be rotated to afford the various surgical pathways to the patient's spine.

As depicted in FIGS. 1-5, for example, the offset main beam 12 includes a forward portion 72 and a rear portion 74. The forward portion 72 supports the head support 20, the arm supports 22A and 22B, the torso-lift support 24, and the coronal adjustment assembly 34, and the rear portion 74 supports the sagittal adjustment assembly 28. The forward and rear portions 72 and 74 are connected to one another by connection member 76 shared therebetween. The forward portion 72 includes a first portion 80, a second portion 82, a third portion 84, and a fourth portion 86. The first portion 80 extends transversely to the axis of rotation of the offset main beam 12, and the second and fourth portions 82 and 86 are aligned with the axis of rotation of the offset main beam 12. The rear portion 74 includes a first portion 90, a second portion 92, and a third portion 94. The first and third portions 90 and 94 are aligned with the axis of rotation of the offset main beam 12, and the second portion 92 extends transversely to the axis of rotation of the offset main beam 12.

The axles 66 are attached to the first portion 80 of the forward portion 72 and to the third portion 94 of the rear portion 74. The lengths of the first portion 80 of the forward portion 72 and the second portion 92 of the rear portion 74 serve in offsetting portions of the forward and rear portions 72 and 74 from the axis of rotation of the offset main beam 12. This offset affords positioning of the cranial-caudal axis of patient P approximately aligned with the axis of rotation of the offset main beam 12.

Programmable settings controlled by a computer controller (not shown) can be used to maintain an ideal patient height for a working position of the surgical frame 10 at a near-constant position through rotation cycles, for example, between the patient positions depicted in FIGS. 1 and 5. This allows for a variable axis of rotation between the first portion 40 and the second portion 42.

Figure 6:
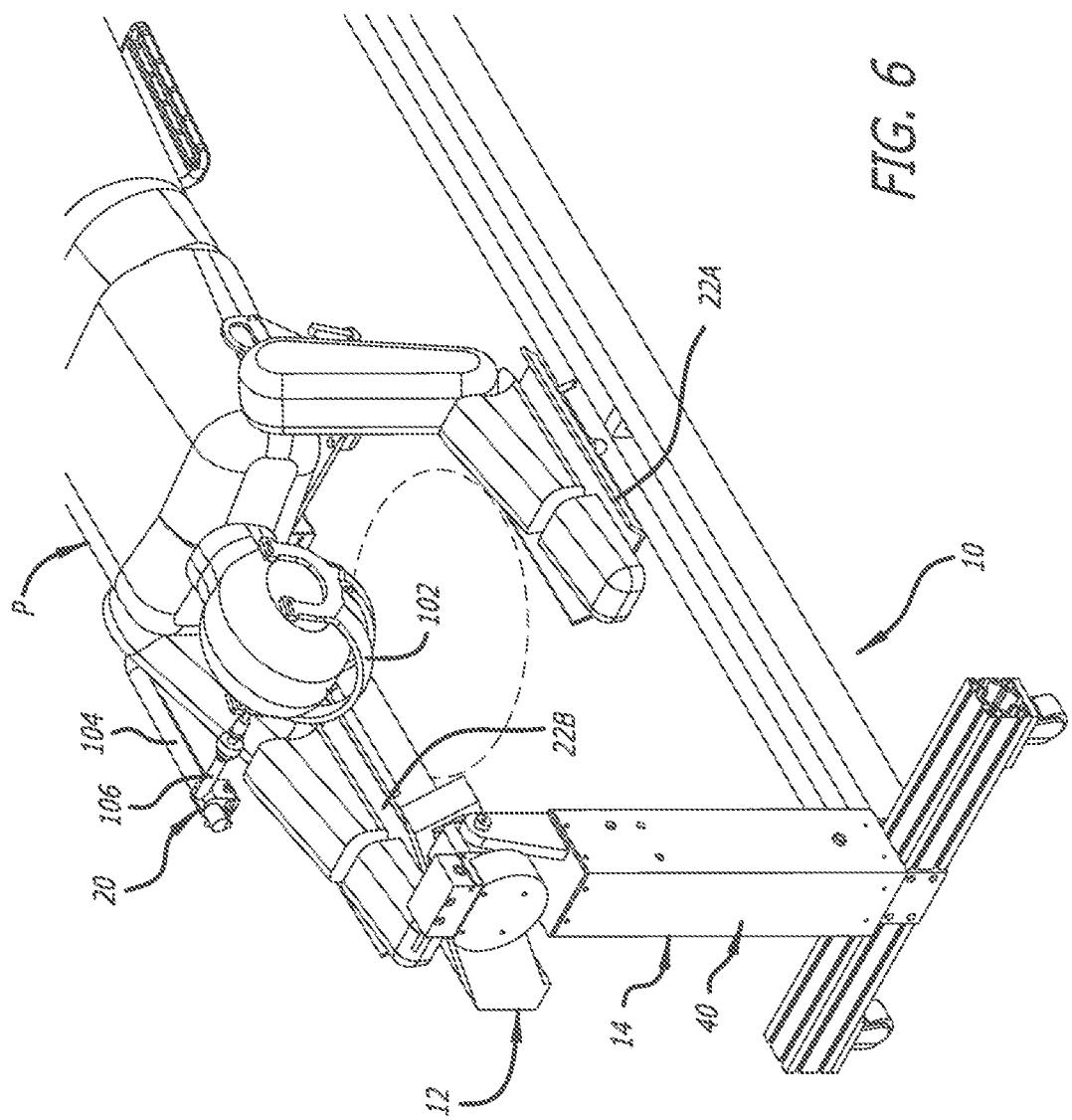
FIG. 6 is a top perspective view of portions of the surgical frame of FIG. 1 showing an area of access to the head of the patient positioned thereon in a prone position.

As depicted in FIG. 5, for example, the head support 20 is attached to a chest support plate 100 of the torso-lift support 24 to support the head of the patient P. If the torso-lift support 24 is not used, the head support 20 can be directly attached to the forward portion 72 of the offset main beam 12. As depicted in FIGS. 4 and 6, for example, the head support 20 further includes a facial support cradle 102, an axially adjustable head support beam 104, and a temple support portion 106. Soft straps (not shown) can be used to secure the patient P to the head support 20. The facial support cradle 102 includes padding across the forehead and cheeks, and provides open access to the mouth of the patient P. The head support 20 also allows for imaging access to the cervical spine. Adjustment of the head support 20 is possible via adjusting the angle and the length of the head support beam 104 and the temple support portion 106.

As depicted in FIG. 5, for example, the arm supports 22A and 22B contact the forearms and support the remainder of the arms of the patient P, with the first arm support 22A and the second arm support 22B attached to the chest support plate 100 of the torso-lift support 24. If the torso-lift support 24 is not used, the arm supports 22A and 22B can both be directly attached to the offset main beam 12. The arm supports 22A and 22B are positioned such that the arms of the patient P are spaced away from the remainder of the patient's body to provide access (FIG. 6) to at least portions of the face and neck of the patient P, thereby providing greater access to the patient.

Figure 7:
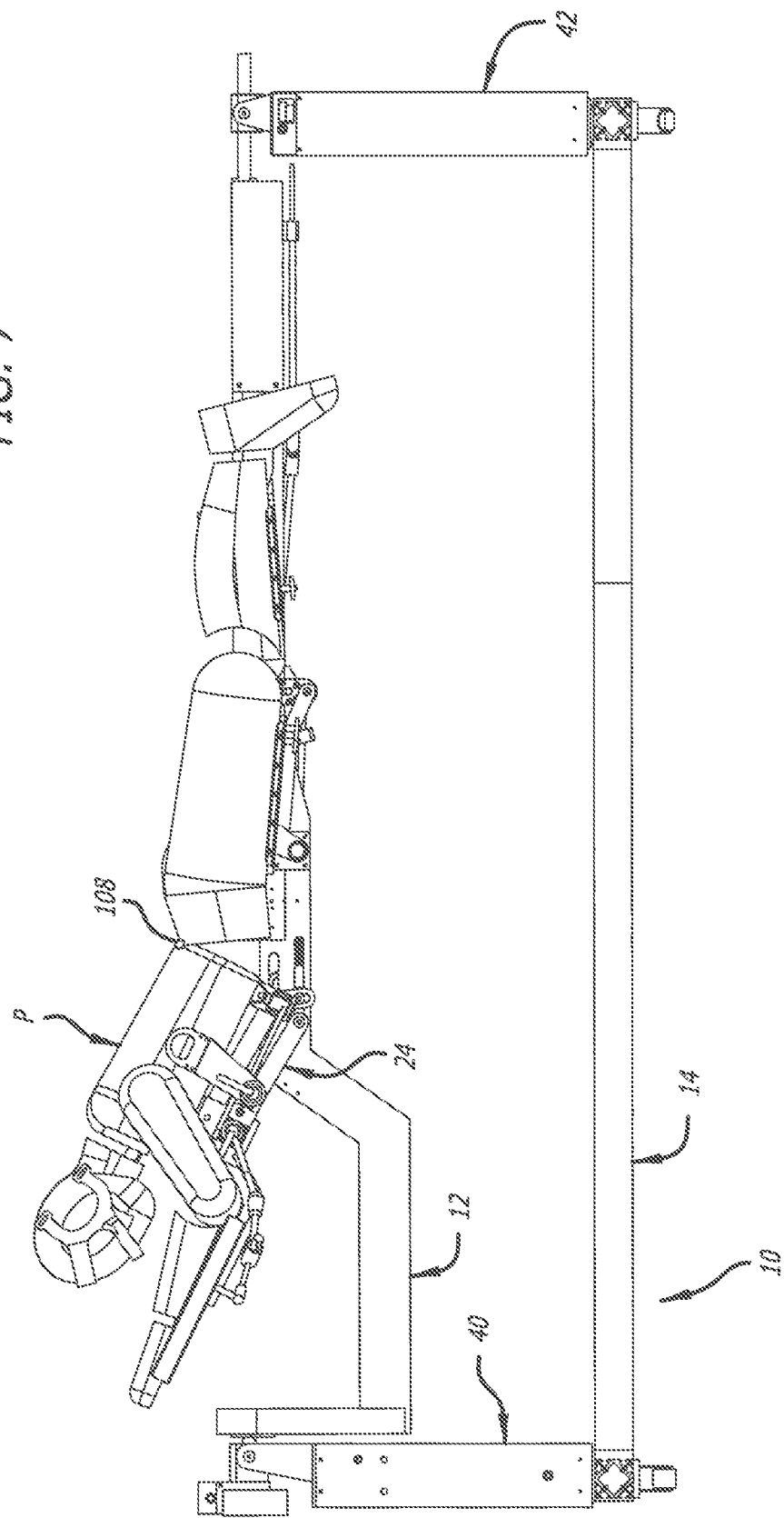
FIG. 7 is a side elevational view of the surgical frame of FIG. 1 showing a torso-lift support supporting the patient in a lifted position.
Figure 8:
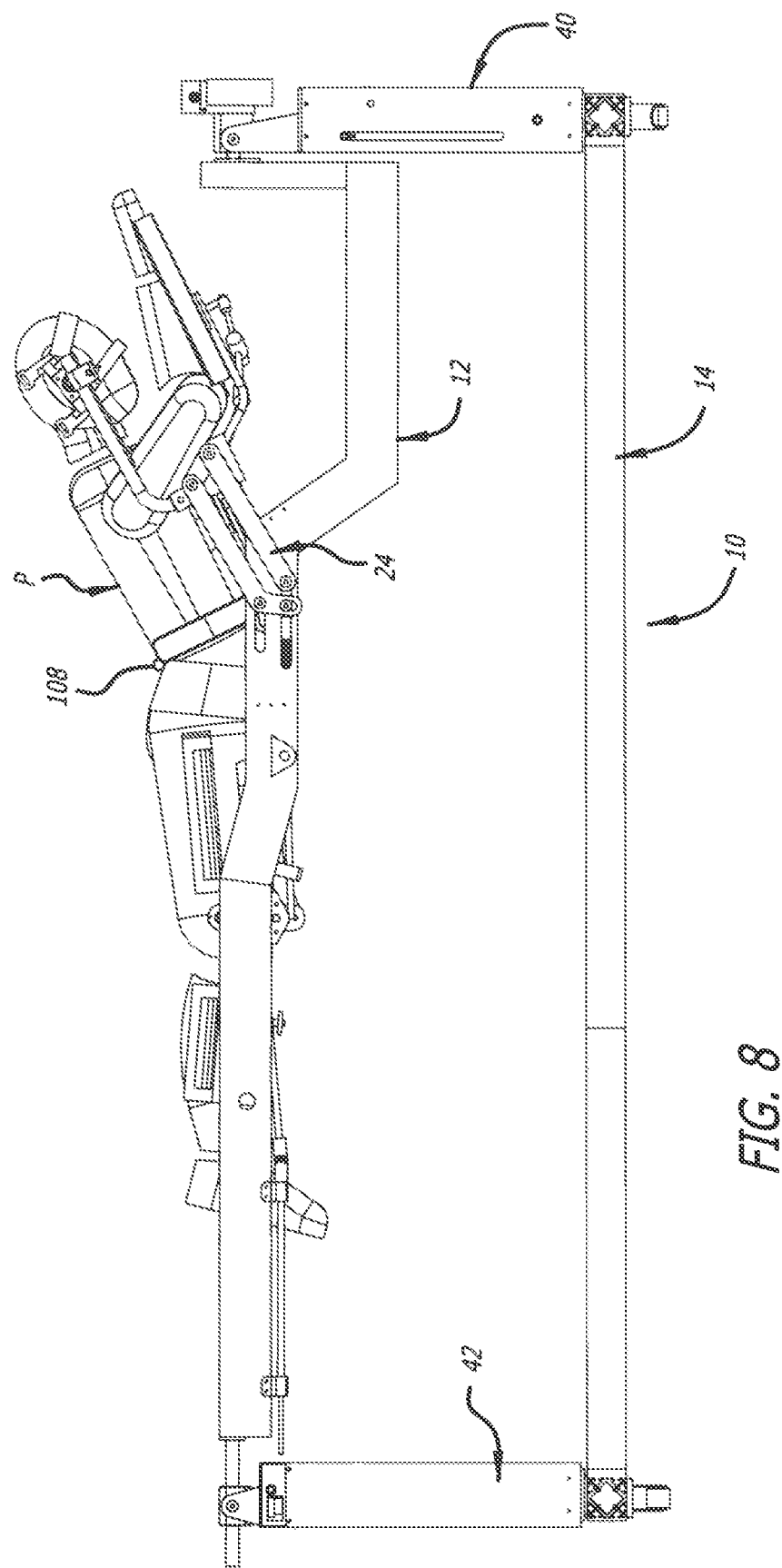
FIG. 8 is another side elevational view of the surgical frame of FIG. 1 showing the torso-lift support supporting the patient in the lifted position.
Figure 9:
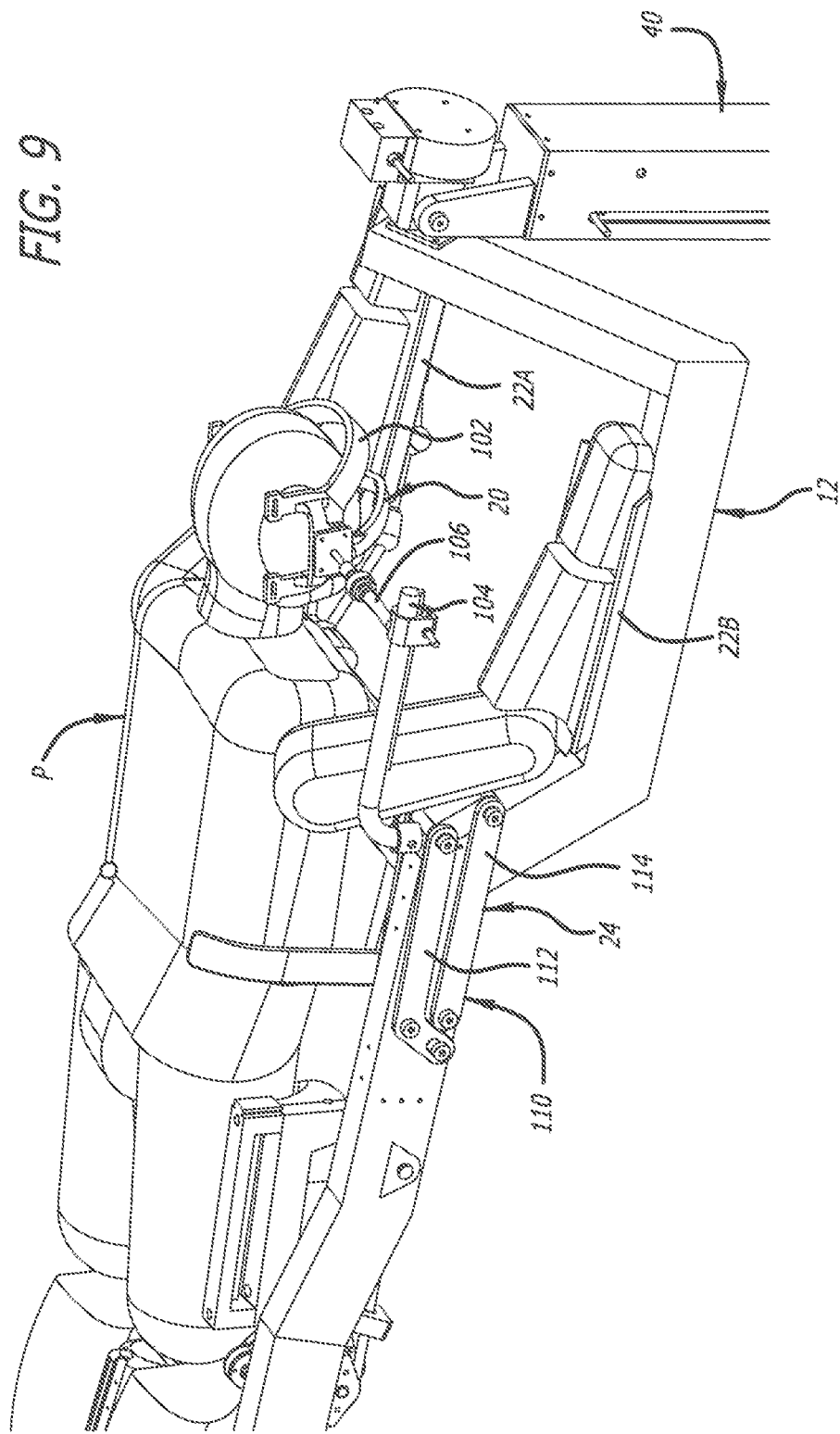
FIG. 9 is an enlarged top perspective view of portions of the surgical frame of FIG. 1 showing the torso-lift support supporting the patient in an unlifted position.

As depicted in FIGS. 7-12, for example, the surgical frame 10 includes a torso-lift capability for lifting and lowering the torso of the patient P between an uplifted position and a lifted position, which is described in detail below with respect to the torso-lift support 24. As depicted in FIGS. 7 and 8, for example, the torso-lift capability has an approximate center of rotation ("COR") 108 that is located at a position anterior to the patient's spine about the L2 of the lumbar spine, and is capable of elevating the upper body of the patient at least an additional six inches when measured at the chest support plate 100.

As depicted in FIGS. 9-12, for example, the torso-lift support 24 includes a "crawling" four-bar mechanism 110 attached to the chest support plate 100. Soft straps (not shown) can be used to secure the patient P to the chest support plate 100. The head support 20 and the arm supports 22A and 22B are attached to the chest support plate 100, thereby moving with the chest support plate 100 as the chest support plate 100 is articulated using the torso-lift support 24. The fixed COR 108 is defined at the position depicted in FIGS. 7 and 8. Appropriate placement of the COR 108 is important so that spinal cord integrity is not compromised (i.e., overly compressed or stretched) during the lift maneuver performed by the torso-lift support 24.

Figure 10:
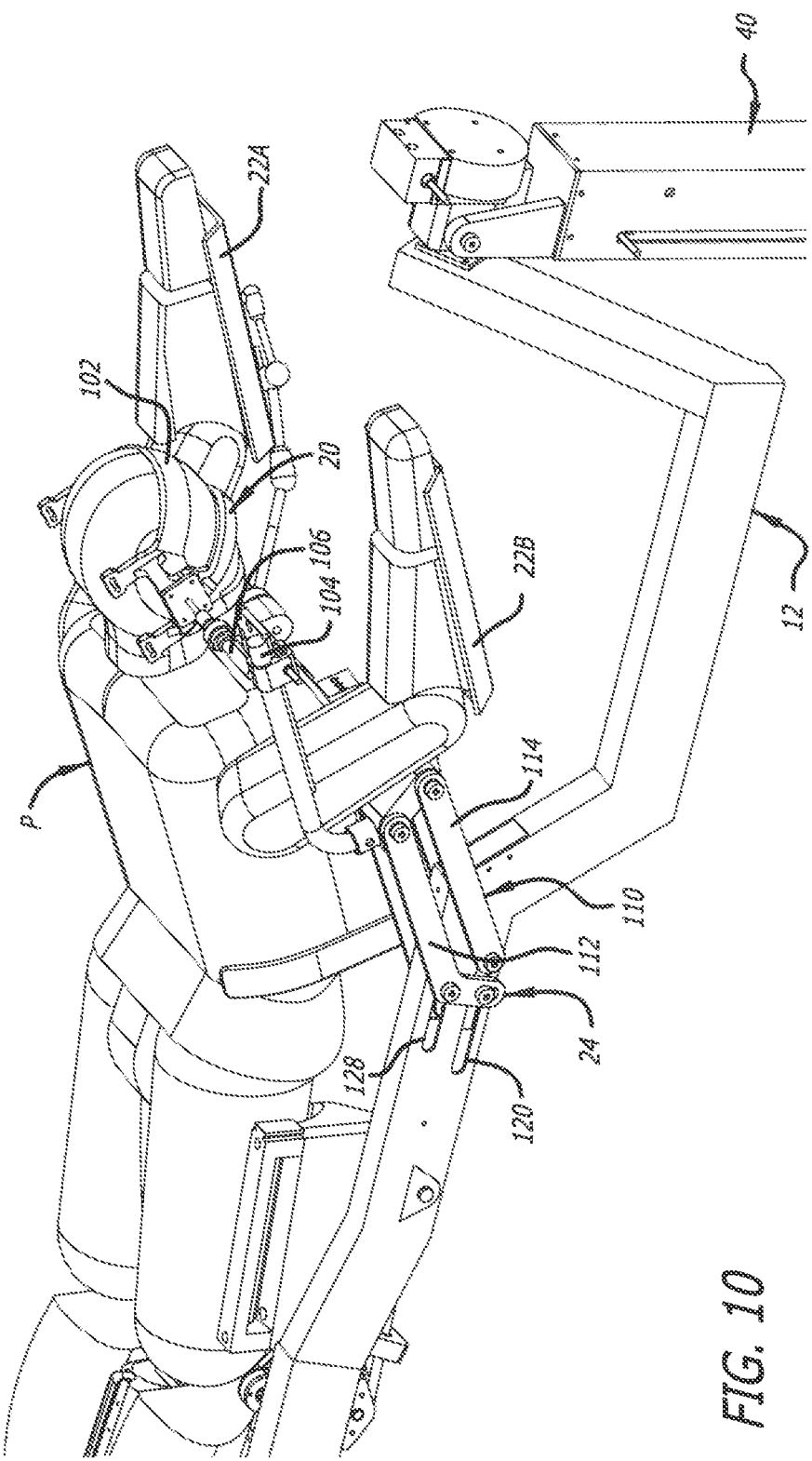
FIG. 10 is an enlarged top perspective view of portions of the surgical frame of FIG. 1 showing the torso-lift support supporting the patient in the lifted position.
Figure 11:
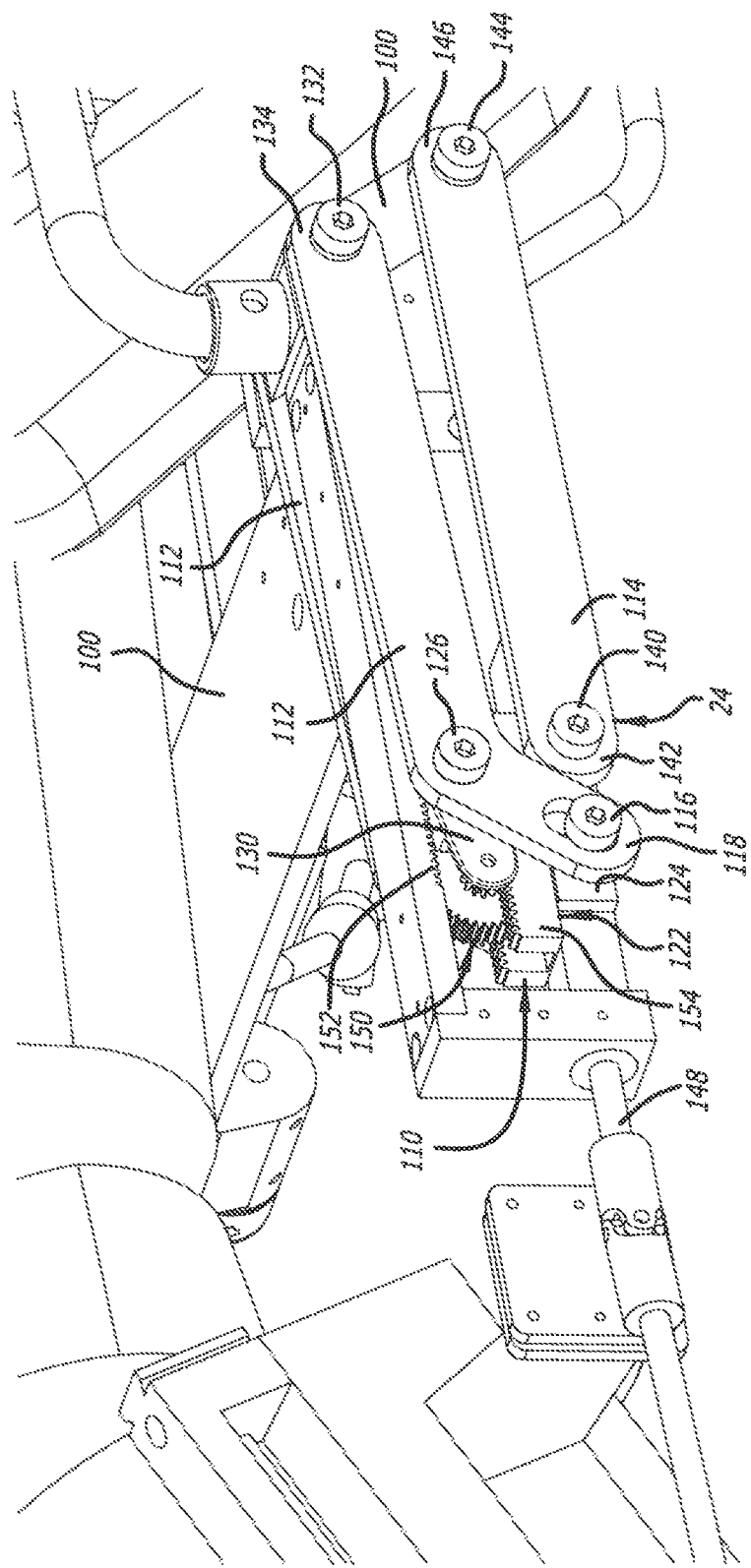
FIG. 11 is an enlarged top perspective view of componentry of the torso-lift support in the unlifted position.

As depicted in FIGS. 10-12, for example, the four-bar mechanism 110 includes first links 112 pivotally connected between offset main beam 12 and the chest support plate 100, and second links 114 pivotally connected between the offset main beam 12 and the chest support plate 100. As depicted in FIGS. 11 and 12, for example, in order to maintain the COR 108 at the desired fixed position, the first and second links 112 and 114 of the four-bar mechanism 110 crawl toward the first support portion 40 of the support structure 14, when the patient's upper body is being lifted. The first and second links 112 and 114 are arranged such that neither the surgeon's workspace nor imaging access are compromised while the patient's torso is being lifted.

As depicted in FIGS. 11 and 12, for example, each of the first links 112 define an L-shape, and includes a first pin 116 at a first end 118 thereof. The first pin 116 extends through first elongated slots 120 defined in the offset main beam 12, and the first pin 116 connects the first links 112 to a dual rack and pinion mechanism 122 via a drive nut 124 provided within the offset main beam 12, thus defining a lower pivot point thereof. Each of the first links 112 also includes a second pin 126 positioned proximate the corner of the L-shape. The second pin 126 extends through second elongated slots 128 defined in the offset main beam 12, and is linked to a carriage 130 of rack and pinion mechanism 122. Each of the first links 112 also includes a third pin 132 at a second end 134 that is pivotally attached to chest support plate 100, thus defining an upper pivot point thereof.

As depicted in FIGS. 11 and 12, for example, each of the second links 114 includes a first pin 140 at a first end 142 thereof. The first pin 140 extends through the first elongated slot 120 defined in the offset main beam 12, and the first pin 140 connects the second links 114 to the drive nut 124 of the rack and pinion mechanism 122, thus defining a lower pivot point thereof. Each of the second links 114 also includes a second pin 144 at a second end 146 that is pivotally connected to the chest support plate 100, thus defining an upper pivot point thereof.

As depicted in FIGS. 11 and 12, the rack and pinion mechanism 122 includes a drive screw 148 engaging the drive nut 124. Coupled gears 150 are attached to the carriage 130. The larger of the gears 150 engage an upper rack 152 (fixed within the offset main beam 12), and the smaller of the gears 150 engage a lower rack 154. The carriage 130 is defined as a gear assembly that floats between the two racks 152 and 154.

As depicted in FIGS. 11 and 12, the rack and pinion mechanism 122 converts rotation of the drive screw 148 into linear translation of the first and second links 112 and 114 in the first and second elongated slots 120 and 128 toward the first portion 40 of the support structure 14. As the drive nut 124 translates along drive screw 148 (via rotation of the drive screw 148), the carriage 130 translates towards the first portion 40 with less travel due to the different gear sizes of the coupled gears 150. The difference in travel, influenced by different gear ratios, causes the first links 112 pivotally attached thereto to lift the chest support plate 100. Lowering of the chest support plate 100 is accomplished by performing this operation in reverse. The second links 114 are "idler" links (attached to the drive nut 124 and the chest support plate 100) that controls the tilt of the chest support plate 100 as it is being lifted and lowered. All components associated with lifting while tilting the chest plate predetermine where COR 108 resides. Furthermore, a servomotor (not shown) interconnected with the drive screw 148 can be computer controlled and/or operated by the operator of the surgical frame 10 to facilitate controlled lifting and lowering of the chest support plate 100. A safety feature can be provided, enabling the operator to read and limit a lifting and lowering force applied by the torso-lift support 24 in order to prevent injury to the patient P. Moreover, the torso-lift support 24 can also include safety stops (not shown) to prevent over-extension or compression of the patient P, and sensors (not shown) programmed to send patient position feedback to the safety stops.

Figure 13A:
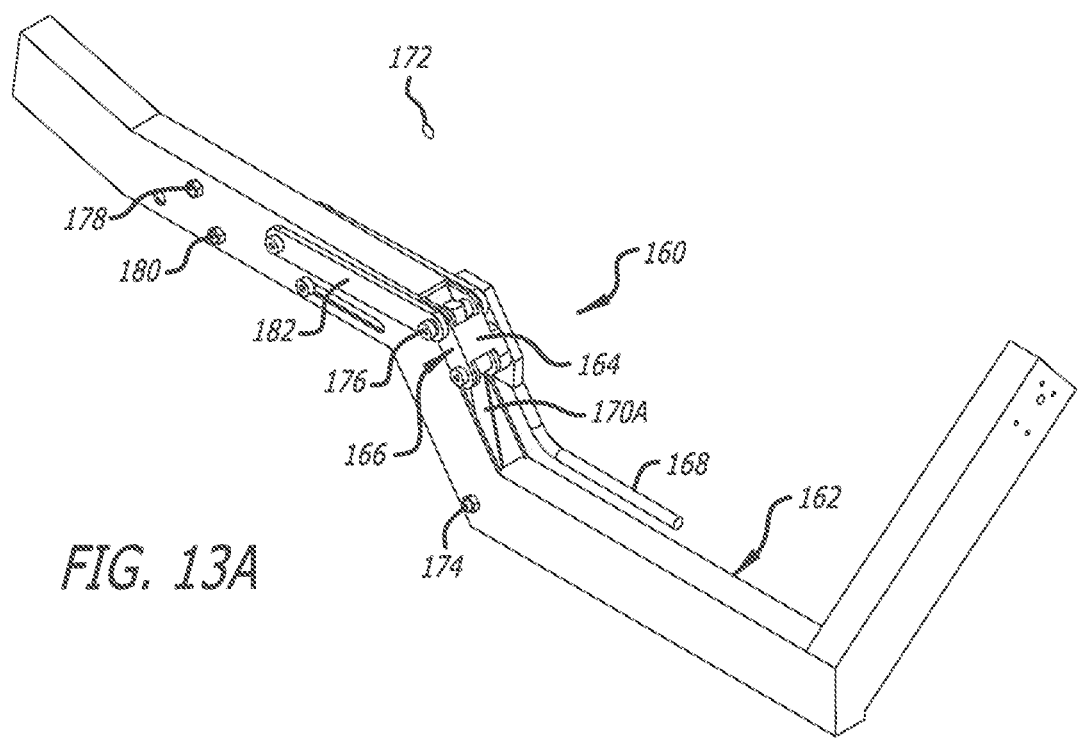
FIG. 13A is a perspective view of an embodiment of a structural offset main beam for use with another embodiment of a torso-lift support showing the torso-lift support in a retracted position.

An alternative preferred embodiment of a torso-lift support is generally indicated by the numeral 160 in FIGS. 13A-15. As depicted in FIGS. 13A-13C, an alternate offest main beam 162 is utilized with the torso-lift support 160. Furthermore, the torso-lift support 160 has a support plate 164 pivotally linked to the offset main beam 162 by a chest support lift mechanism 166. An arm support rod/plate 168 is connected to the support plate 164, and the second arm support 22B. The support plate 164 is attached to the chest support plate 100, and the chest support lift mechanism 166 includes various actuators 170A, 170B, and 170C used to facilitate positioning and repositioning of the support plate 164 (and hence, the chest support plate 100).

Figure 13B:
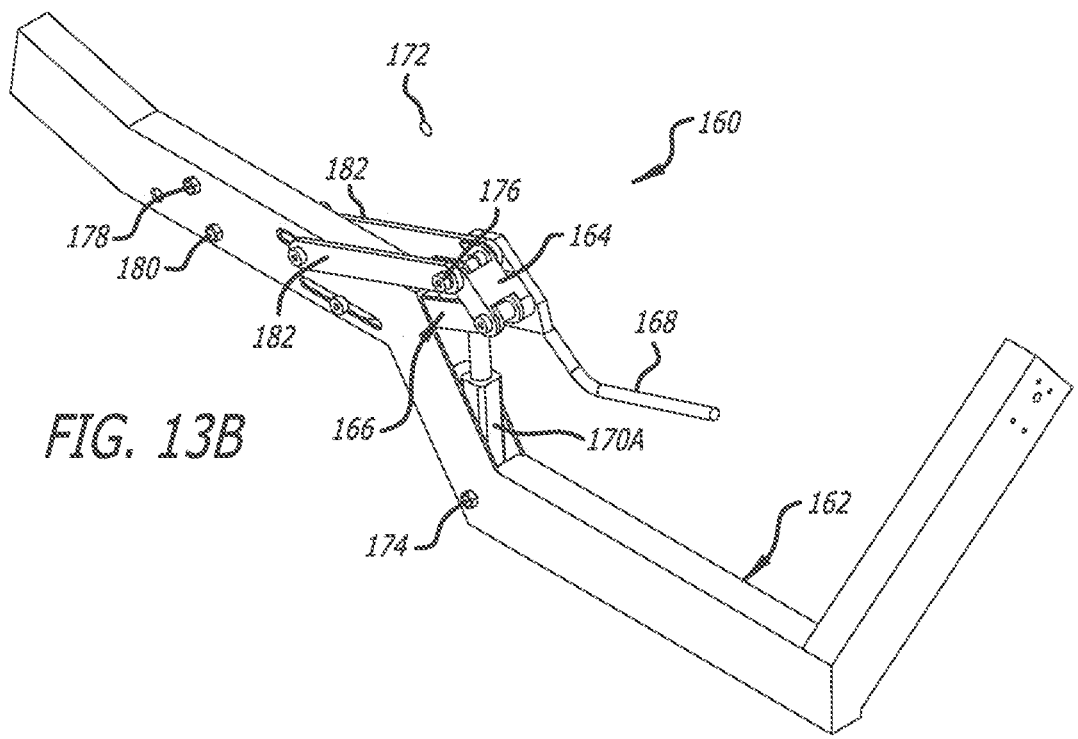
FIG. 13B is a perspective view similar to FIG. 13A showing the torso-lift support at half travel.
Figure 13C:
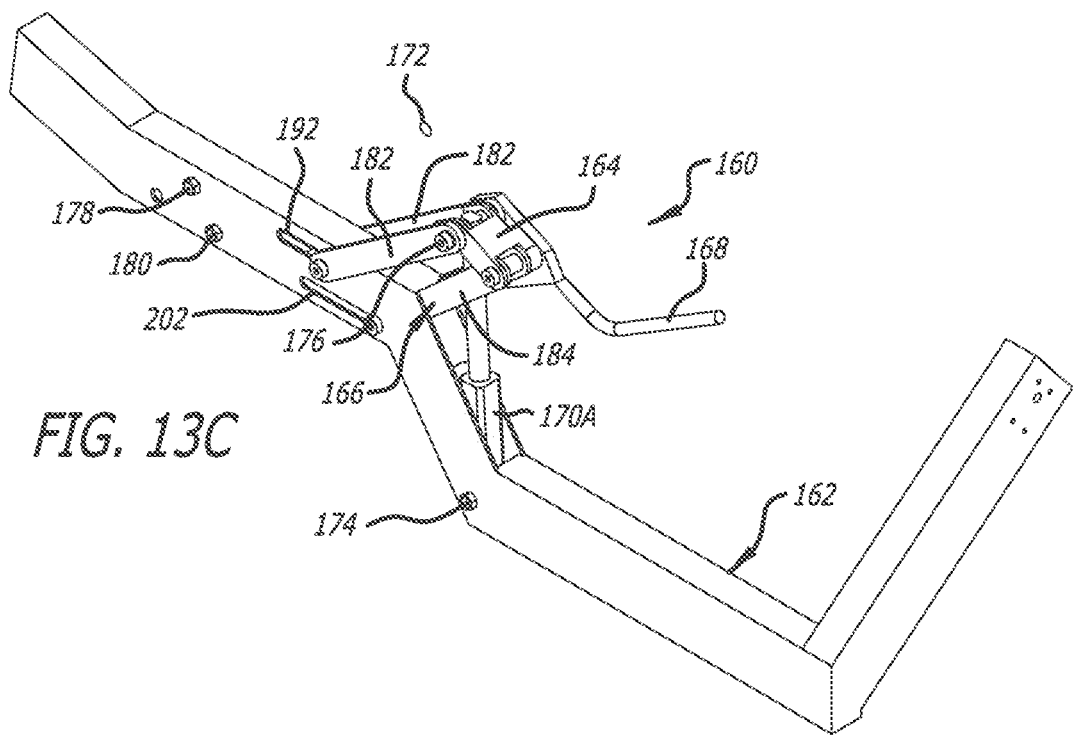
FIG. 13C is a perspective view similar to FIGS. 13A and 13B showing the torso-lift support at full travel.

As discussed below, the torso-lift support 160 depicted in FIGS. 13A-15 enables a COR 172 thereof to be programmably altered such that the COR 172 can be a fixed COR or a variable COR. As their names suggest, the fixed COR stays in the same position as the torso-lift support 160 is actuated, and the variable COR moves between a first position and a second position as the torso-lift support 160 is actuated between its initial position and final position at full travel thereof. Appropriate placement of the COR 172 is important so that spinal cord integrity is not compromised (i.e., overly compressed or stretched). Thus, the support plate 164 (and hence, the chest support plate 100) follows a path coinciding with a predetermined COR 172 (either fixed or variable). FIG. 13A depicts the torso-lift support 160 retracted, FIG. 13B depicts the torso-lift support 160 at half travel, and FIG. 13C depicts the torso-lift support 160 at full travel.

Figure 15:
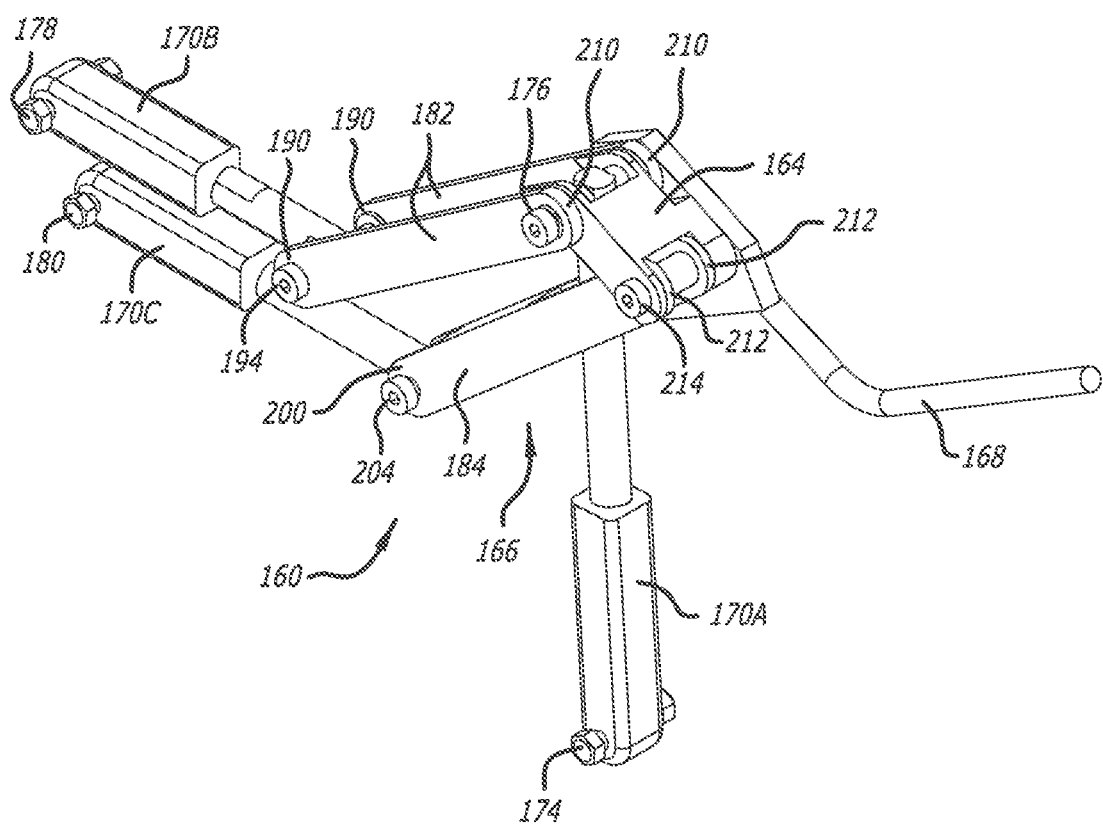
FIG. 15 is another perspective view of a chest support lift mechanism of the torso-lift support of FIGS. 13A-13C with the actuators thereof extended.

As discussed above, the chest support lift mechanism 166 includes the actuators 170A, 170B, and 170C to position and reposition the support plate 164 (and hence, the chest support plate 100). As depicted in FIGS. 14 and 15, for example, the first actuator 170A, the second actuator 170B, and the third actuator 170C are provided. Each of the actuators 170A, 170B, and 170C are interconnected with the offset main beam 12 and the support plate 164, and each of the actuators 170A, 170B, and 170C are moveable between a retracted and extended position. As depicted in FIGS. 13A-13C, the first actuator 170A is pinned to the offset main beam 162 using a pin 174 and pinned to the support plate 164 using a pin 176. Furthermore, the second and third actuators 170B and 170C are received within the offset main beam 162. The second actuator 170B is interconnected with the offset main beam 162 using a pin 178, and the third actuator 170C is interconnected with the offset main beam 162 using a pin 180.

The second actuator 170B is interconnected with the support plate 164 via first links 182, and the third actuator 170C is interconnected with the support plate 164 via second links 184. First ends 190 of the first links 182 are pinned to the second actuator 170B and elongated slots 192 formed in the offset main beam 162 using a pin 194, and first ends 200 of the second links 184 are pinned to the third actuator 170C and elongated slots 202 formed in the offset main beam 162 using a pin 204. The pins 194 and 204 are moveable within the elongated slots 192 and 202. Furthermore, second ends 210 of the first links 182 are pinned to the support plate 164 using the pin 176, and second ends 212 of the second links 184 are pinned to the support plate 164 using a pin 214. To limit interference therebetween, as depicted in FIGS. 13A-13C, the first links 182 are provided on the exterior of the offset main beam 162, and, depending on the position thereof, the second links 184 are positioned on the interior of the offset main beam 162.

Actuation of the actuators 170A, 170B, and 170C facilitates movement of the support plate 164. Furthermore, the amount of actuation of the actuators 170A, 170B, and 170C can be varied to affect different positions of the support plate 164. As such, by varying the amount of actuation of the actuators 170A, 170B, and 170C, the COR 172 thereof can be controlled. As discussed above, the COR 172 can be predetermined, and can be either fixed or varied. Furthermore, the actuation of the actuators 170A, 170B, and 170C can be computer controlled and/or operated by the operator of the surgical frame 10, such that the COR 172 can be programmed by the operator. As such, an algorithm can be used to determine the rates of extension of the actuators 170A, 170B, and 170C to control the COR 172, and the computer controls can handle implementation of the algorithm to provide the predetermined COR. A safety feature can be provided, enabling the operator to read and limit a lifting force applied by the actuators 170A, 170B, and 170C in order to prevent injury to the patient P. Moreover, the torso-lift support 160 can also include safety stops (not shown) to prevent over-extension or compression of the patient P, and sensors (not shown) programmed to send patient position feedback to the safety stops.

FIGS. 16-23 depict portions of the sagittal adjustment assembly 28. The sagittal adjustment assembly 28 can be used to distract or compress the patient's lumbar spine during or after lifting or lowering of the patient's torso by the torso-lift supports. The sagittal adjustment assembly 28 supports and manipulates the lower portion of the patient's body. In doing so, the sagittal adjustment assembly 28 is configured to make adjustments in the sagittal plane of the patient's body, including tilting the pelvis, controlling the position of the upper and lower legs, and lordosing the lumbar spine.

Figure 16:
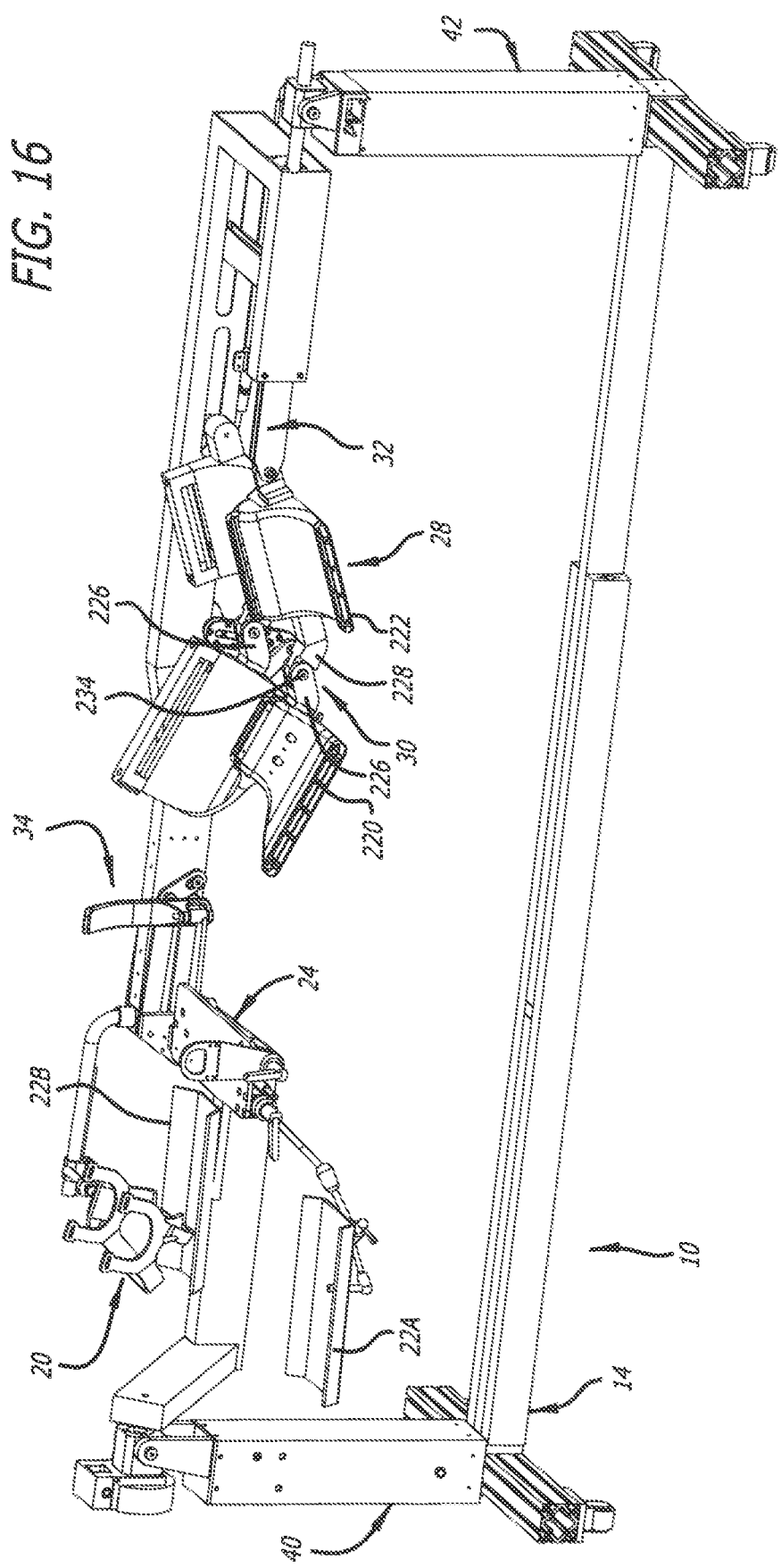
FIG. 16 is a top perspective view of the surgical frame of FIG. 5.
Figure 17:
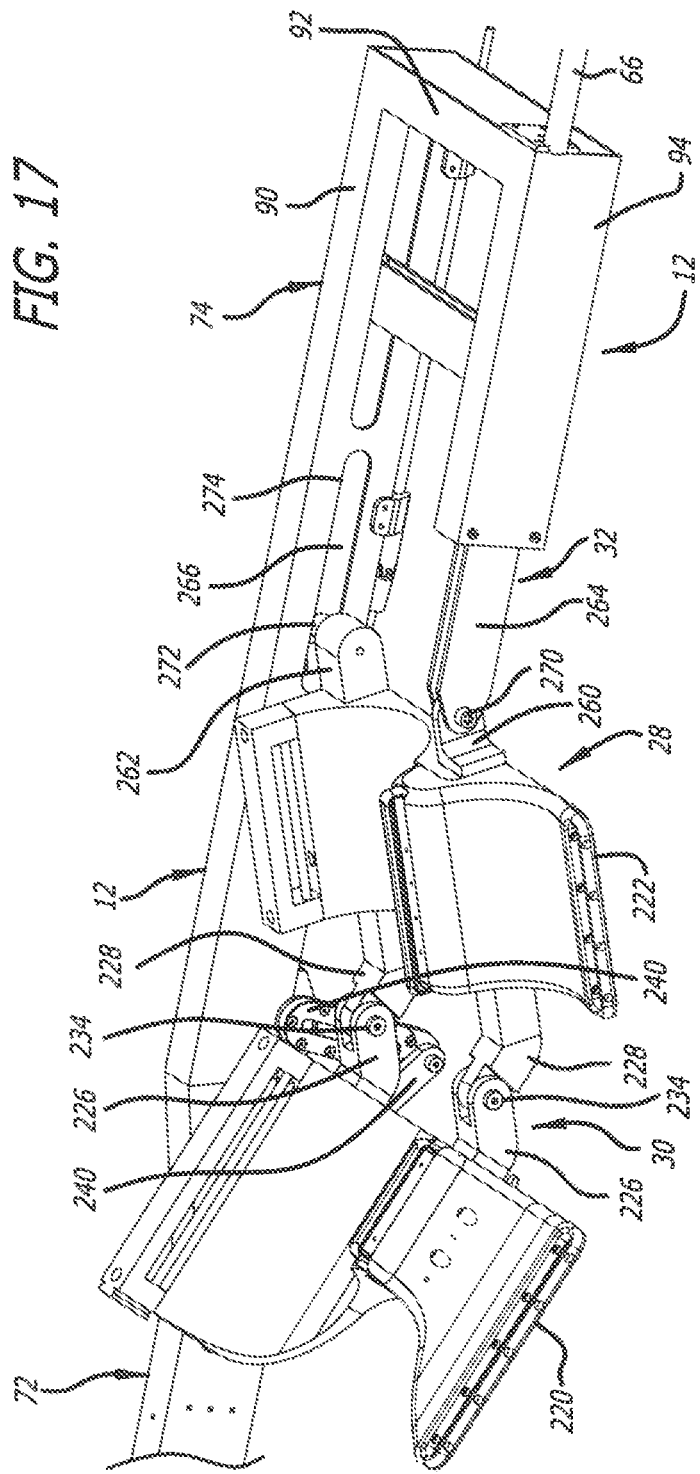
FIG. 17 is an enlarged top perspective view of portions of the surgical frame of FIG. 1 showing a sagittal adjustment assembly including a pelvic-tilt mechanism and leg adjustment mechanism.

As depicted in FIGS. 16 and 17, for example, the sagittal adjustment assembly 28 includes the pelvic-tilt mechanism 30 for supporting the thighs and lower legs of the patient P. The pelvic-tilt mechanism 30 includes a thigh cradle 220 configured to support the patient's thighs, and a lower leg cradle 222 configured to support the patient's shins. Different sizes of thigh and lower leg cradles can be used to accommodate different sizes of patients, i.e., smaller thigh and lower leg cradles can be used with smaller patients, and larger thigh and lower leg cradles can be used with larger patients. Soft straps (not shown) can be used to secure the patient P to the thigh cradle 220 and the lower leg cradle 222. The thigh cradle 220 and the lower leg cradle 222 are moveable and pivotal with respect to one another and to the offset main beam 12. To facilitate rotation of the patient's hips, the thigh cradle 220 and the lower leg cradle 222 can be positioned anterior and inferior to the patient's hips.

Figure 18:
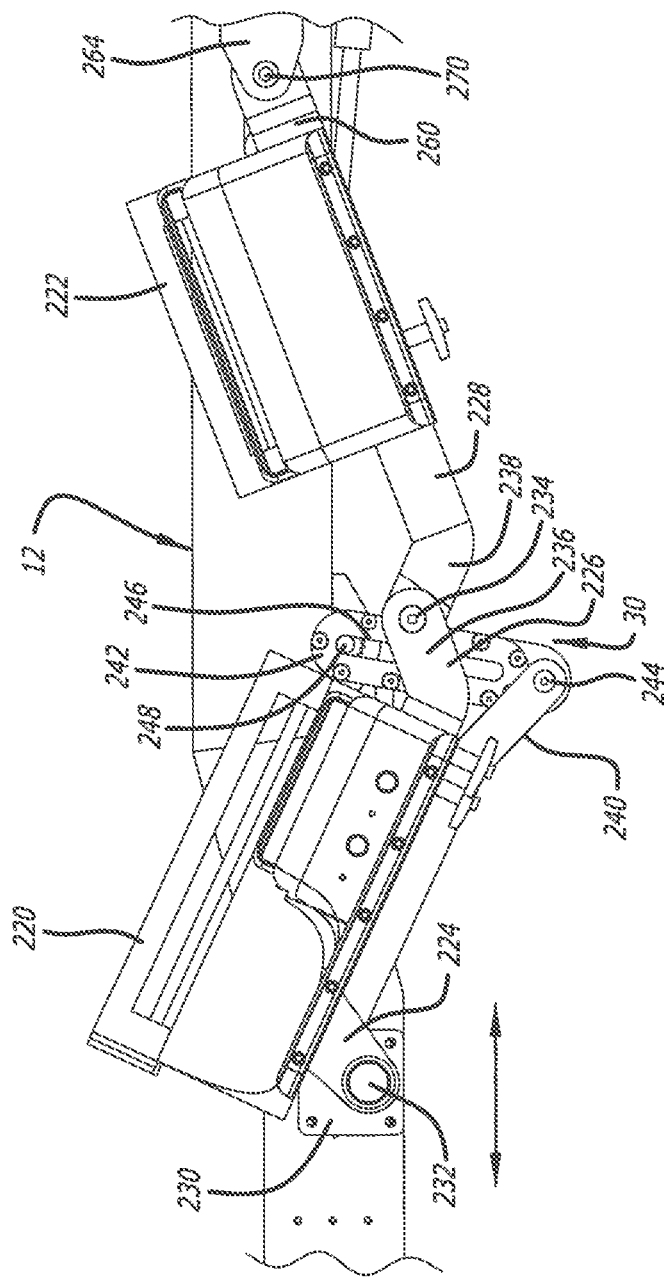
FIG. 18 is an enlarged side elevational view of portions of the surgical frame of FIG. 1 showing the pelvic-tilt mechanism.
Figure 25:
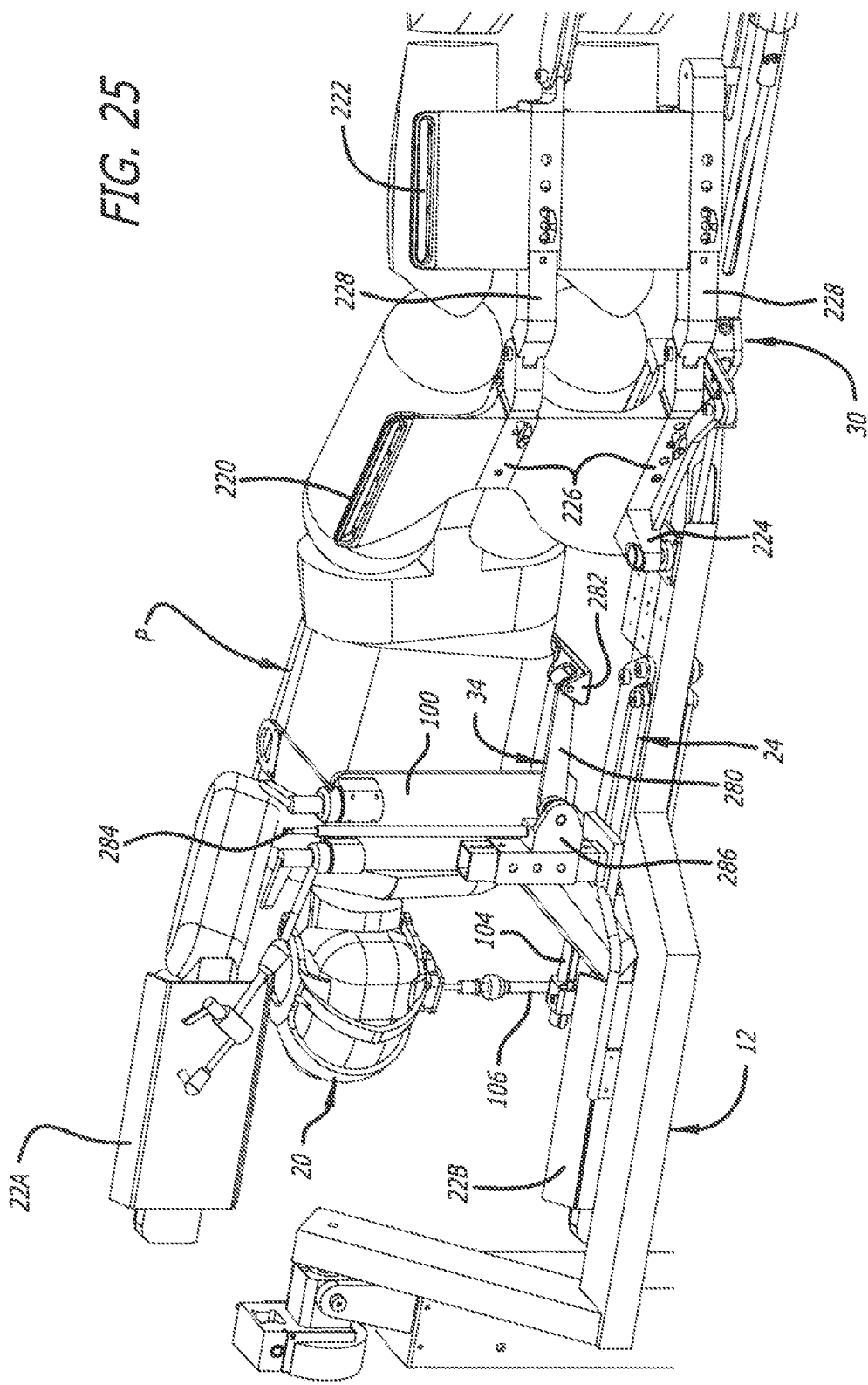
FIG. 25 is a top perspective view of portions of the surgical frame of FIG. 1 showing operation of the coronal adjustment assembly.

As depicted in FIGS. 18 and 25, for example, a first support strut 224 and second support struts 226 are attached to the thigh cradle 220. Furthermore, third support struts 228 are attached to the lower leg cradle 222. The first support strut 224 is pivotally attached to the offset main beam 12 via a support plate 230 and a pin 232, and the second support struts 226 are pivotally attached to the third support struts 228 via pins 234. The pins 234 extend through angled end portions 236 and 238 of the second and third support struts 226 and 228, respectively. Furthermore, the lengths of second and third support struts 226 and 228 are adjustable to facilitate expansion and contraction of the lengths thereof.

To accommodate patients with different torso lengths, the position of the thigh cradle 220 can be adjustable by moving the support plate 230 along the offset main beam 12. Furthermore, to accommodate patients with different thigh and lower leg lengths, the lengths of the second and third support struts 226 and 228 can be adjusted.

Figure 19:
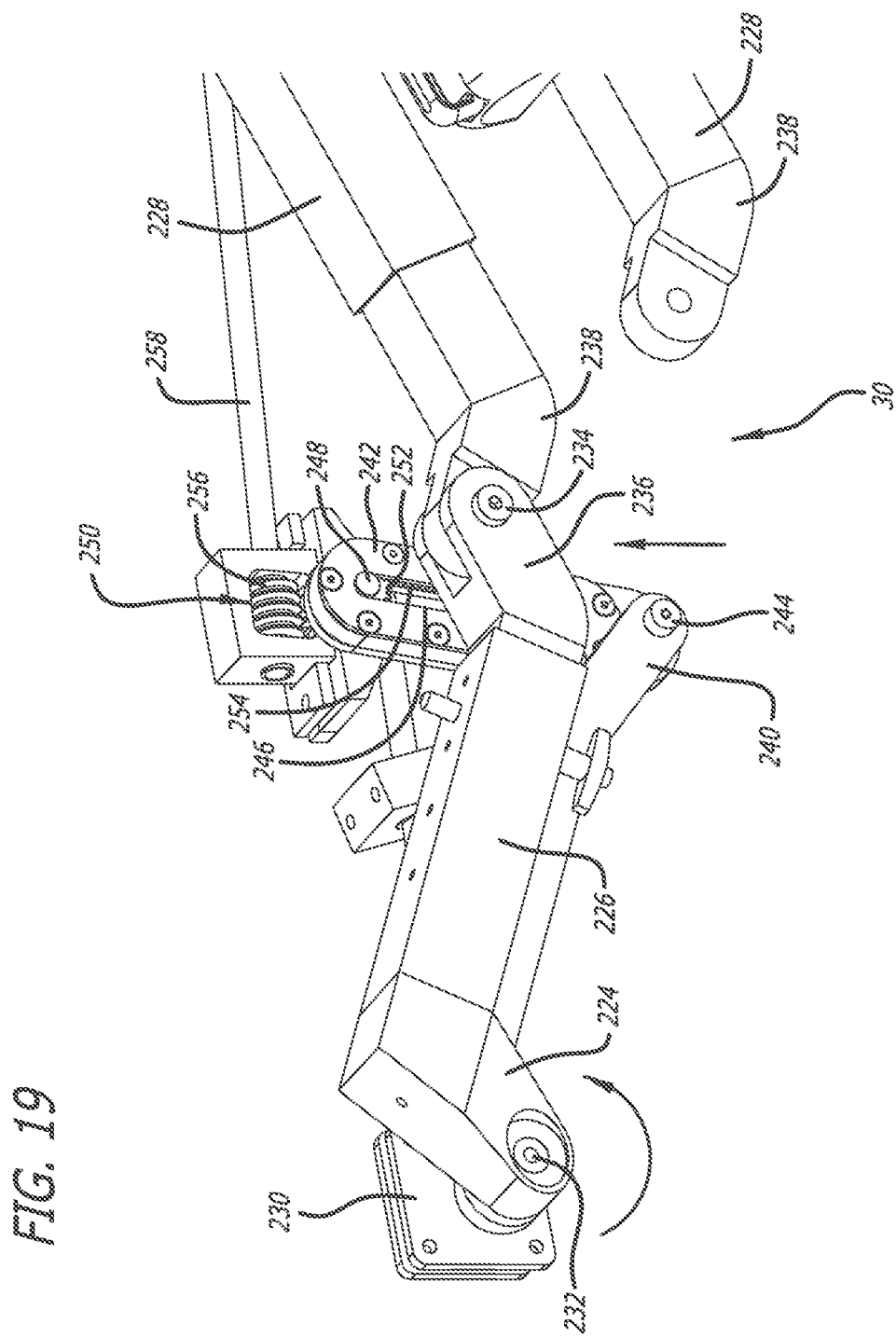
FIG. 19 is an enlarged perspective view of componentry of the pelvic-tilt mechanism.
Figure 20:
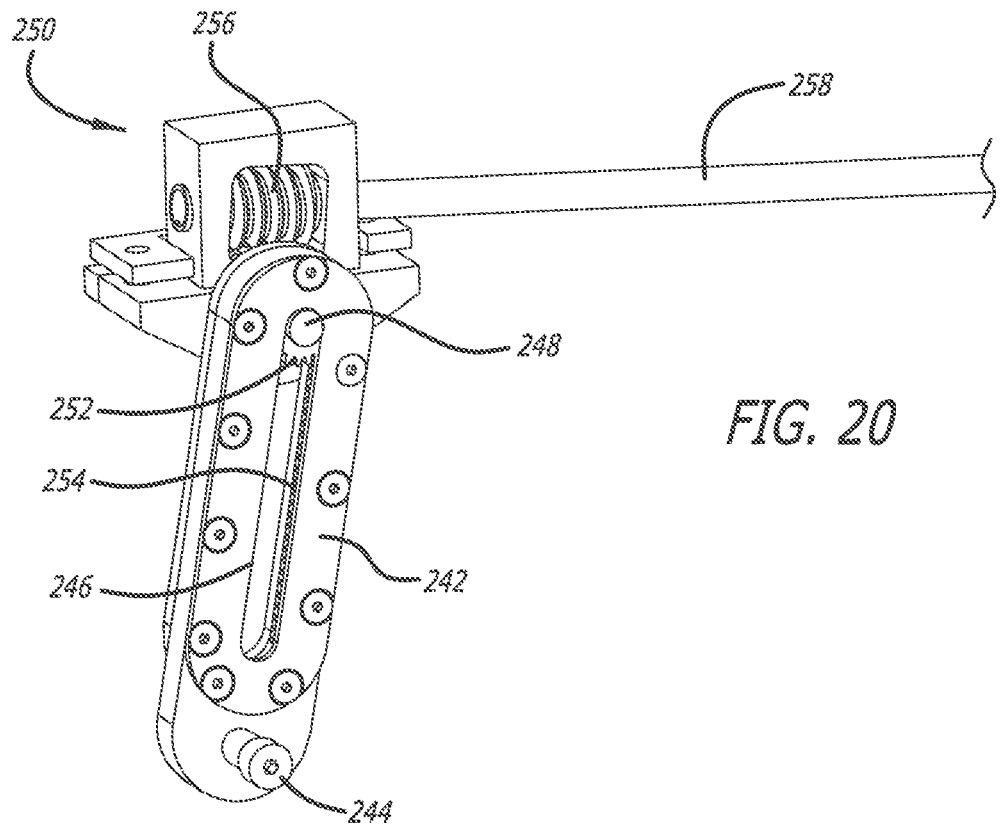
FIG. 20 is an enlarged perspective view of a captured rack and a worm gear assembly of the componentry of the pelvic-tilt mechanism.
Figure 21:
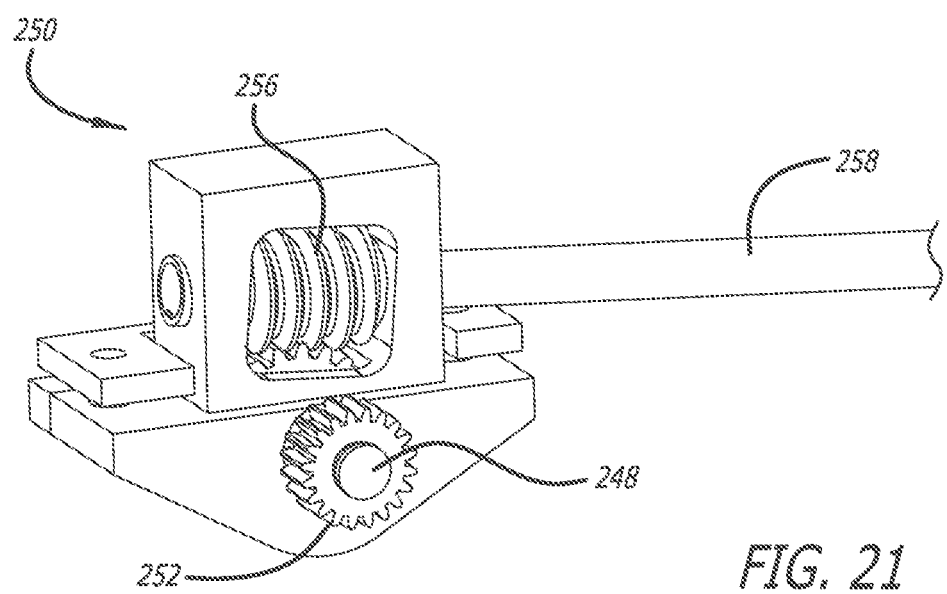
FIG. 21 is an enlarged perspective view of the worm gear assembly of FIG. 20.

To control the pivotal angle between the second and third support struts 226 and 228 (and hence, the pivotal angle between the thigh cradle 220 and lower leg cradle 222), a link 240 is pivotally connected to a captured rack 242 via a pin 244. The captured rack 242 includes an elongated slot 246, through which is inserted a worm gear shaft 248 of a worm gear assembly 250. The worm gear shaft 248 is attached to a gear 252 provided on the interior of the captured rack 242. The gear 252 contacts teeth 254 provided inside the captured rack 242, and rotation of the gear 252 (via contact with the teeth 254) causes motion of the captured rack 242 upwardly and downwardly. The worm gear assembly 250, as depicted in FIGS. 19-21, for example, includes worm gears 256 which engage a drive shaft 258, and which are connected to the worm gear shaft 248.

The worm gear assembly 250 also is configured to function as a brake, which prevents unintentional movement of the sagittal adjustment assembly 28. Rotation of the drive shaft 258 causes rotation of the worm gears 256, thereby causing reciprocal vertical motion of the captured rack 242. The vertical reciprocal motion of the captured rack 242 causes corresponding motion of the link 240, which in turn pivots the second and third support struts 226 and 228 to correspondingly pivot the thigh cradle 220 and lower leg cradle 222. A servomotor (not shown) interconnected with the drive shaft 258 can be computer controlled and/or operated by the operator of the surgical frame 10 to facilitate controlled reciprocal motion of the captured rack 242.

The sagittal adjustment assembly 28 also includes the leg adjustment mechanism 32 facilitating articulation of the thigh cradle 220 and the lower leg cradle 222 with respect to one another. In doing so, the leg adjustment mechanism 32 accommodates the lengthening and shortening of the patient's legs during bending thereof. As depicted in FIG. 17, for example, the leg adjustment mechanism 32 includes a first bracket 260 and a second bracket 262 attached to the lower leg cradle 222. The first bracket 260 is attached to a first carriage portion 264, and the second bracket 262 is attached to a second carriage portion 266 via pins 270 and 272, respectively. The first carriage portion 264 is slidable within third portion 94 of the rear portion 74 of the offset main beam 12, and the second carriage portion 266 is slidable within the first portion 90 of the rear portion 74 of the offset main beam 12. An elongated slot 274 is provided in the first portion 90 to facilitate engagement of the second bracket 262 and the second carriage portion 266 via the pin 272. As the thigh cradle 220 and the lower leg cradle 222 articulate with respect to one another (and the patient's legs bend accordingly), the first carriage 264 and the second carriage 266 can move accordingly to accommodate such movement.

Figure 22:
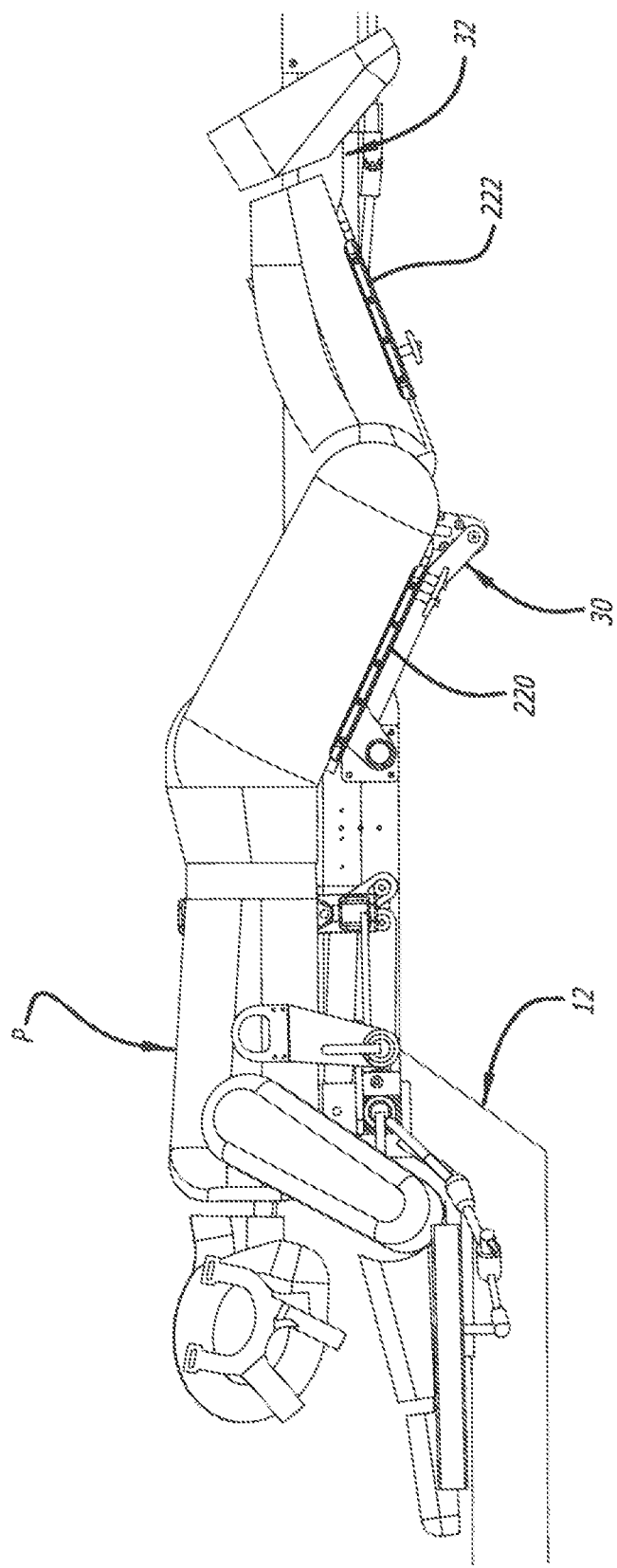
FIG. 22 is a side elevational view of portions of the surgical frame of FIG. 1 showing the patient positioned thereon and the pelvic-tilt mechanism of the sagittal adjustment assembly in the flexed position.
Figure 23:
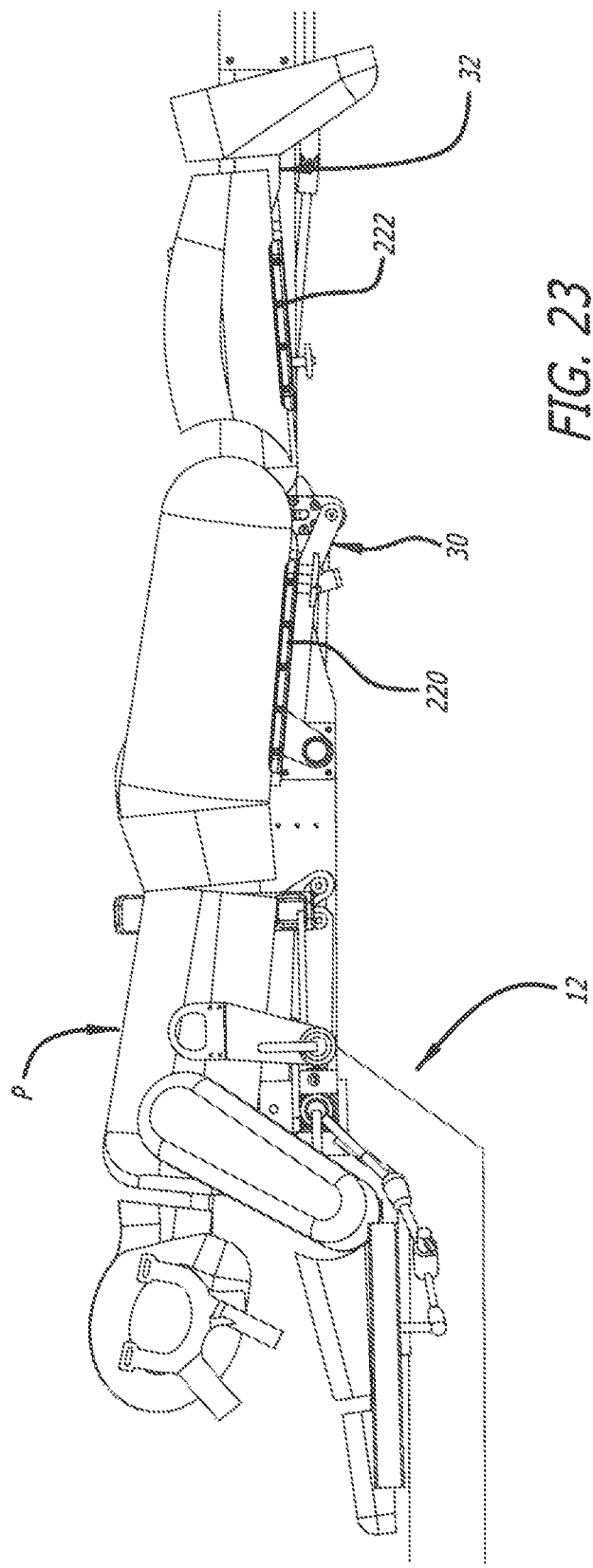
FIG. 23 is another side elevational view of portions of the surgical frame of FIG. 1 showing the patient positioned thereon and the pelvic-tilt mechanism of the sagittal adjustment assembly in the fully extended position.

The pelvic-tilt mechanism 30 is movable between a flexed position and a fully extended position. As depicted in FIG. 22, in the flexed position, the lumbar spine is hypo-lordosed. This opens the posterior boundaries of the lumbar vertebral bodies and allows for easier placement of any interbody devices. The lumbar spine stretches slightly in this position. As depicted in FIG. 23, in the extended position, the lumbar spine is lordosed. This compresses the lumbar spine. When posterior fixation devices, such as rods and screws, are placed, optimal sagittal alignment can be achieved. During sagittal alignment, little to negligible angle change occurs between the thighs and the pelvis. The pelvic-tilt mechanism 30 also can hyper-extend the hips as a means of lordosing the spine, in addition to tilting the pelvis. One of ordinary skill will recognize, however, that straightening the patient's legs does not lordose the spine. Leg straightening is a consequence of rotating the pelvis while maintaining a fixed angle between the pelvis and the thighs.

The sagittal adjustment assembly 28, having the configuration described above, further includes an ability to compress and distract the spine dynamically while in the lordosed or flexed positions. The sagittal adjustment assembly 28 also includes safety stops (not shown) to prevent over-extension or compression of the patient, and sensors (not shown) programmed to send patient position feedback to the safety stops.

Figure 24:
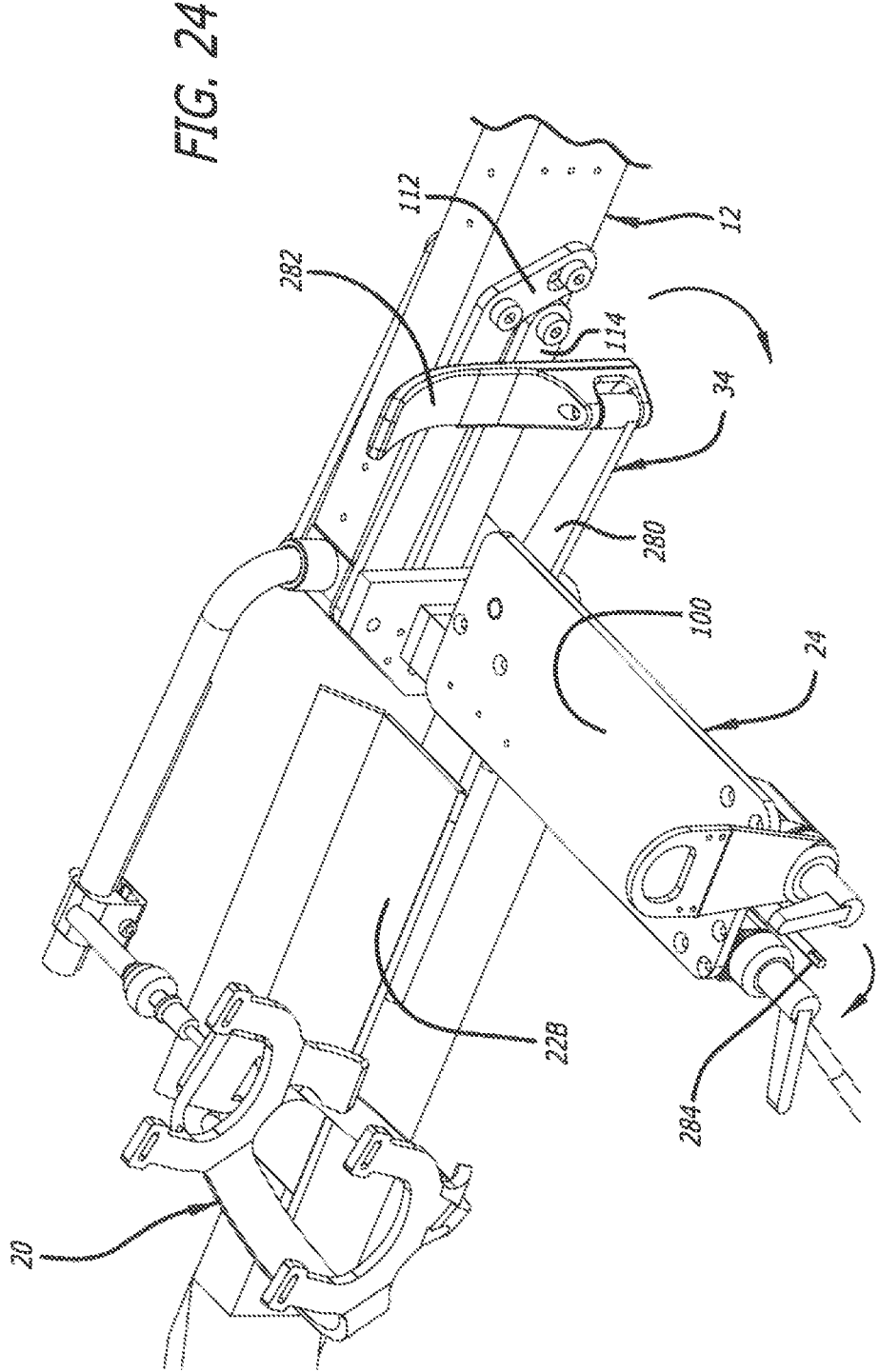
FIG. 24 is an enlarged top perspective view of portions of the surgical frame of FIG. 1 showing a coronal adjustment assembly.
Figure 26:
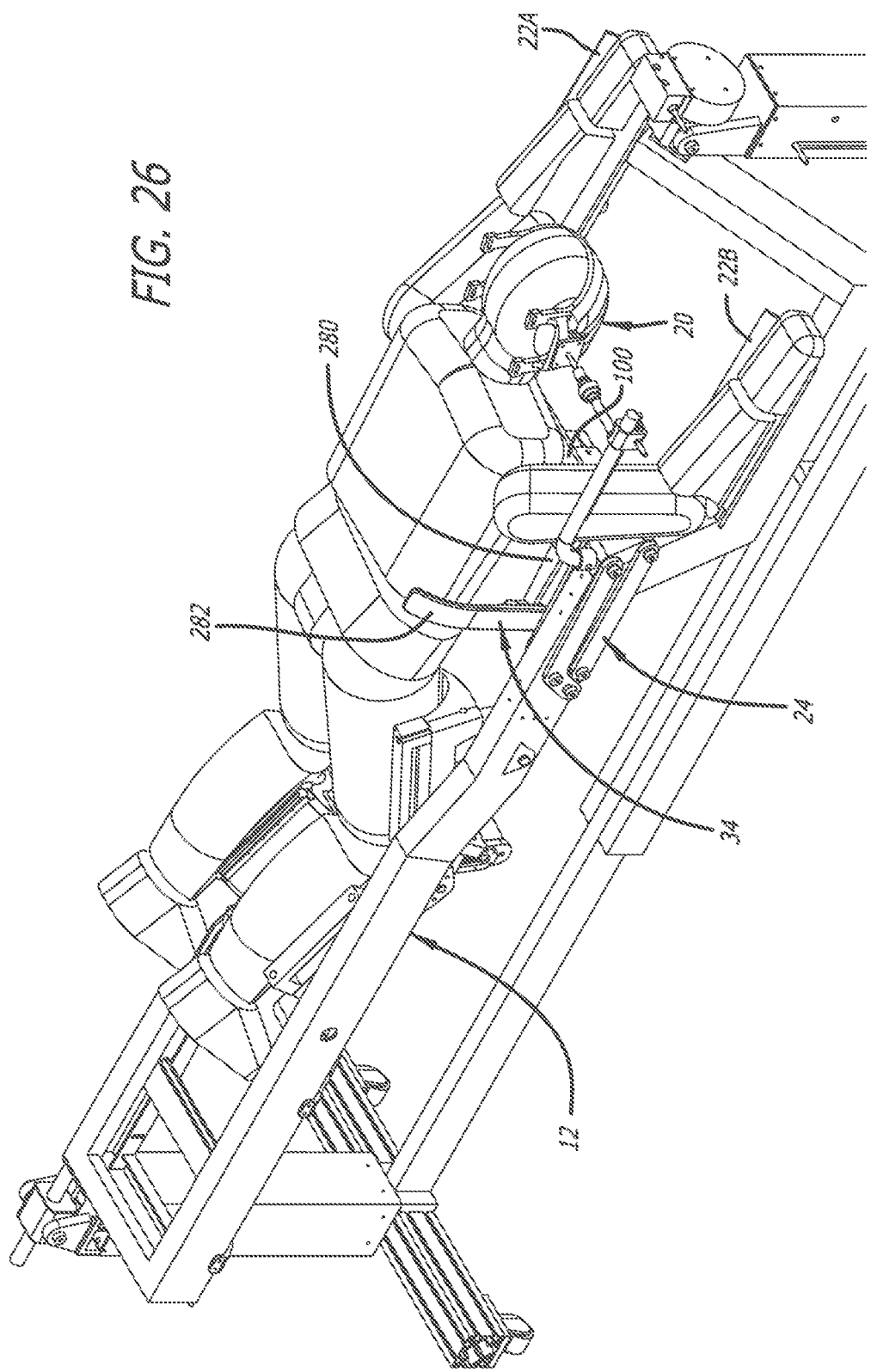
FIG. 26 is a top perspective view of a portion of the surgical frame of FIG. 1 showing operation of the coronal adjustment assembly.
Figure 27:
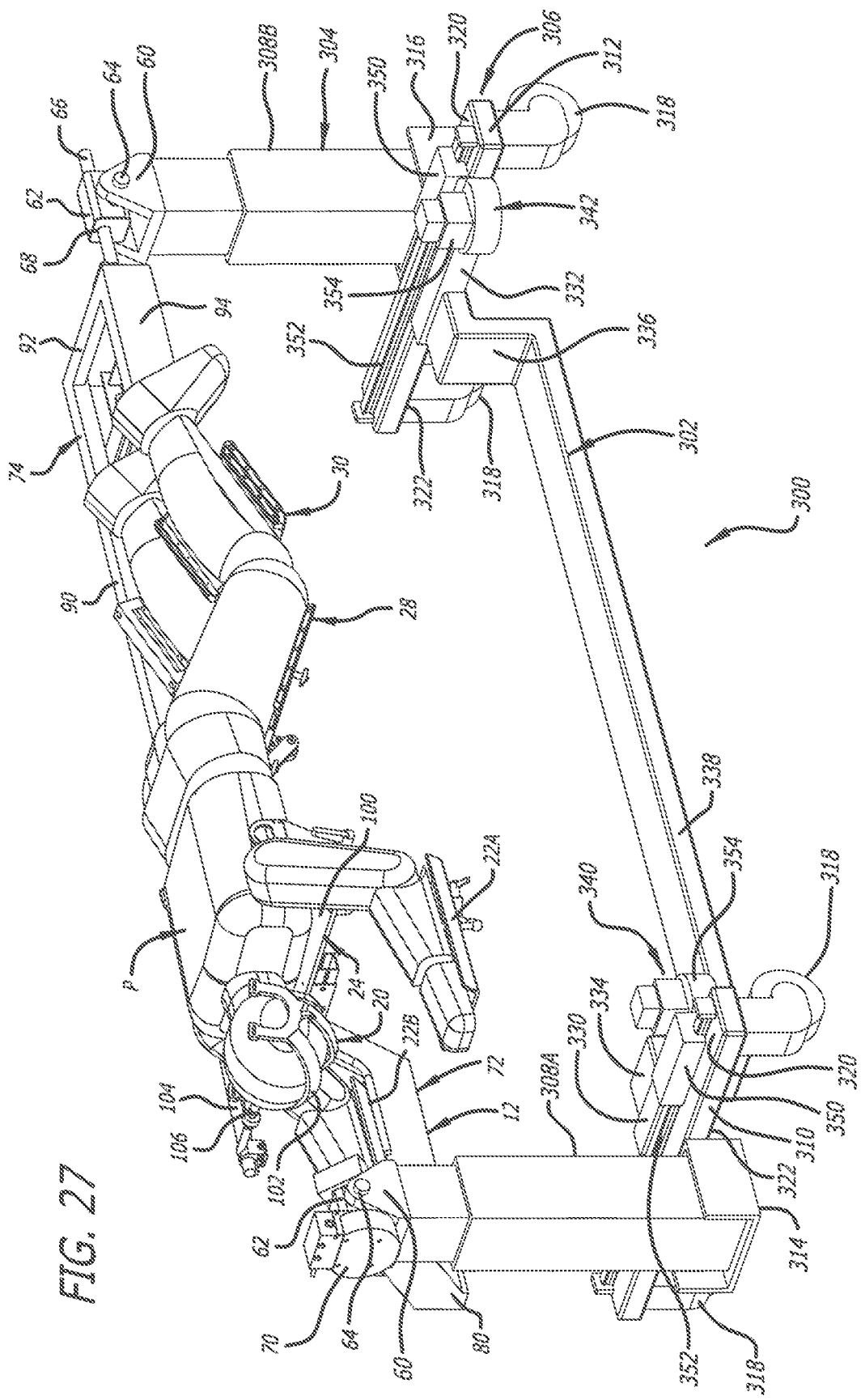
FIG. 27 is a top perspective view of a surgical frame in accordance with an embodiment of the present invention with the patient positioned thereon in a prone position showing a translating beam thereof in a first position.

As depicted in FIGS. 24-26, for example, the coronal adjustment assembly 34 is configured to support and manipulate the patient's torso, and further to correct a spinal deformity, including but not limited to a scoliotic spine. As depicted in FIGS. 24-26, for example, the coronal adjustment assembly 34 includes a lever 280 linked to an arcuate radio-lucent paddle 282. As depicted in FIGS. 24 and 25, for example, a rotatable shaft 284 is linked to the lever 280 via a transmission 286, and the rotatable shaft 284 projects from an end of the chest support plate 100. Rotation of the rotatable shaft 284 is translated by the transmission 286 into rotation of the lever 280, causing the paddle 282, which is linked to the lever 280, to swing in an arc. Furthermore, a servomotor (not shown) interconnected with the rotatable shaft 284 can be computer controlled and/or operated by the operator of the surgical frame 10 to facilitate controlled rotation of the lever 280.

As depicted in FIG. 24, for example, adjustments can be made to the position of the paddle 282 to manipulate the torso and straighten the spine. As depicted in FIG. 25, when the offset main beam 12 is positioned such that the patient P is positioned in a lateral position, the coronal adjustment assembly 34 supports the patient's torso. As further depicted in FIG. 26, when the offset main beam 12 is positioned such that the patient P is positioned in a prone position, the coronal adjustment assembly 34 can move the torso laterally, to correct a deformity, including but not limited to a scoliotic spine. When the patient is strapped in via straps (not shown) at the chest and legs, the torso is relatively free to move and can be manipulated. Initially, the paddle 282 is moved by the lever 280 away from the offset main beam 12. After the paddle 282 has been moved away from the offset main beam 12, the torso can be pulled with a strap towards the offset main beam 12. The coronal adjustment assembly 34 also includes safety stops (not shown) to prevent over-extension or compression of the patient, and sensors (not shown) programmed to send patient position feedback to the safety stops.

A preferred embodiment of a surgical frame incorporating a translating beam is generally indicated by the numeral 300 in FIGS. 27-30. Like the surgical frame 10, the surgical frame 300 serves as an exoskeleton to support the body of the patient P as the patient's body is manipulated thereby. In doing so, the surgical frame 300 serves to support the patient P such that the patient's spine does not experience unnecessary stress/torsion.

The surgical frame 300 includes translating beam 302 that is generally indicated by the numeral 302 in FIGS. 27-30. The translating beam 302 is capable of translating motion affording it to be positioned and repositioned with respect to portions of the remainder of the surgical frame 300. As discussed below, the positioning and repositioning of the translating beam 302, for example, affords greater access to a patient receiving area A defined by the surgical frame 300, and affords greater access to the patient P by a surgeon and/or a surgical assistant (generally indicated by the letter S in FIG. 30) via access to either of the lateral sides $L_1$ and $L_2$ (FIG. 30) of the surgical frame 300.

As discussed below, by affording greater access to the patient receiving area A, the surgical frame 300 affords transfer of the patient P from and to a surgical table/gurney. Using the surgical frame 300, the surgical table/gurney can be conventional, and there is no need to lift the surgical table/gurney over portions of the surgical frame 300 to afford transfer of the patient P thereto.

The surgical frame 300 is configured to provide a relatively minimal amount of structure adjacent the patient's spine to facilitate access thereto and to improve the quality of imaging available before, during, and even after surgery. Thus, the workspace of a surgeon and/or a surgical assistant and imaging access are thereby increased. The workspace, as discussed below, can be further increased by positioning and repositioning the translating beam 302. Furthermore, radio-lucent or low magnetic susceptibility materials can be used in constructing the structural components adjacent the patient's spine in order to further enhance imaging quality.

The surgical frame 300, as depicted in FIGS. 27-30, is similar to the surgical frame 10 except that surgical frame 300 includes a support structure 304 having a support platform 306 incorporating the translating beam 302. The surgical frame 300 incorporates the offset main beam 12 and the features associated therewith from the surgical table 300. As such, the element numbering used to describe the surgical frame 10 is also applicable to portions of the surgical frame 300.

Rather than including the cross member 44, and the horizontal portions 46 and the vertical portions 48 of the first and second support portions 40 and 42, the support structure 304 includes the support platform 306, a first vertical support post 308A, and a second vertical support post 308B. As depicted in FIGS. 27-30, the support platform 306 extends from adjacent one longitudinal end to adjacent the other longitudinal end of the surgical frame 300, and the support platform 306 supports the first vertical support post 308A at the one longitudinal end and supports the second vertical support post 308B at the other longitudinal end.

As depicted in FIGS. 27-30, the support platform 306 (in addition to the translating beam 302) includes a first end member 310, a second end member 312, a first support bracket 314, and a second support bracket 316. Casters 318 are attached to the first and second end members 310 and 312. The first end member 310 and the second end member 312 each include an upper surface 320 and a lower surface 322. The casters 318 can be attached to the lower surface of each of the first and second end members 310 and 312 at each end thereof, and the casters 318 can be spaced apart from one another to afford stable movement of the surgical frame 300. Furthermore, the first support bracket 314 supports the first vertical support post 308A, and the second support bracket 316 supports the vertical second support post 308B.

The translating beam 302 is interconnected with the first and second end members 310 and 312 of the support platform 306, and as depicted in FIGS. 27-30, the translating beam 302 is capable of movement with respect to the first and second end members 310 and 312. The translating beam 302 includes a first end member 330, a second end member 332, a first L-shaped member 334, a second L-shaped member 336, and a cross member 338. The first L-shaped member 334 is attached to the first end member 330 and the cross member 338, and the second L-shaped member 336 is attached to the second end member 332 and the cross member 338. Portions of the first and second L-shaped members 334 and 336 extend downwardly relative to the first and second end members 330 and 332 such that the cross member 338 is positioned vertically below the first and second end member 330 and 332. The vertical position of the cross member 338 relative to the remainder of the surgical frame 300 lowers the center of gravity of the surgical frame 300, and in doing so, serves in adding to the stability of the surgical frame 300.

The translating beam 302, as discussed above, is capable of being positioned and repositioned with respect to portions of the remainder of the surgical frame 300. To that end, the support platform 306 includes a first translation mechanism 340 and a second translation mechanism 342. The first translation mechanism 340 facilitates attachment between the first end members 310 and 330, and the second translation mechanism 342 facilitates attachment between the second end members 312 and 332. The first and second translation mechanism 340 and 342 also facilitate movement of the translating beam 302 relative to the first end member 310 and the second end member 312.

The first and second translation mechanisms 340 and 342 can each include a transmission 350 and a track 352 for facilitating movement of the translating beam 302. The tracks 352 are provided on the upper surface 320 of the first and second end members 310 and 312, and the transmissions 350 are interoperable with the tracks 352. The first and second transmission mechanisms 340 and 342 can each include an electrical motor 354 or a hand crank (not shown) for driving the transmissions 350. Furthermore, the transmissions 350 can include, for example, gears or wheels driven thereby for contacting the tracks 352. The interoperability of the transmissions 350, the tracks 352, and the motors 354 or hand cranks form a drive train for moving the translating beam 302. The movement afforded by the first and second translation mechanism 340 and 342 allows the translating beam 302 to be positioned and repositioned relative to the remainder of the surgical frame 300.

The surgical frame 300 can be configured such that operation of the first and second translation mechanism 340 and 342 can be controlled by an operator such as a surgeon and/or a surgical assistant. As such, movement of the translating beam 302 can be effectuated by controlled automation. Furthermore, the surgical frame 300 can be configured such that movement of the translating beam 302 automatically coincides with the rotation of the offset main beam 12. By tying the position of the translating beam 302 to the rotational position of the offset main beam 12, the center of gravity of the surgical frame 300 can be maintained in positions advantageous to the stability thereof.

During use of the surgical frame 300, access to the patient receiving area A and the patient P can be increased or decreased by moving the translating beam 302 between the lateral sides $L_1$ and $L_2$ of the surgical frame 300. Affording greater access to the patient receiving area A facilitates transfer of the patient P between the surgical table/gurney and the surgical frame 300. Furthermore, affording greater access to the patient P facilitates ease of access by a surgeon and/or a surgical assistant to the surgical site on the patient P.

Figure 28:
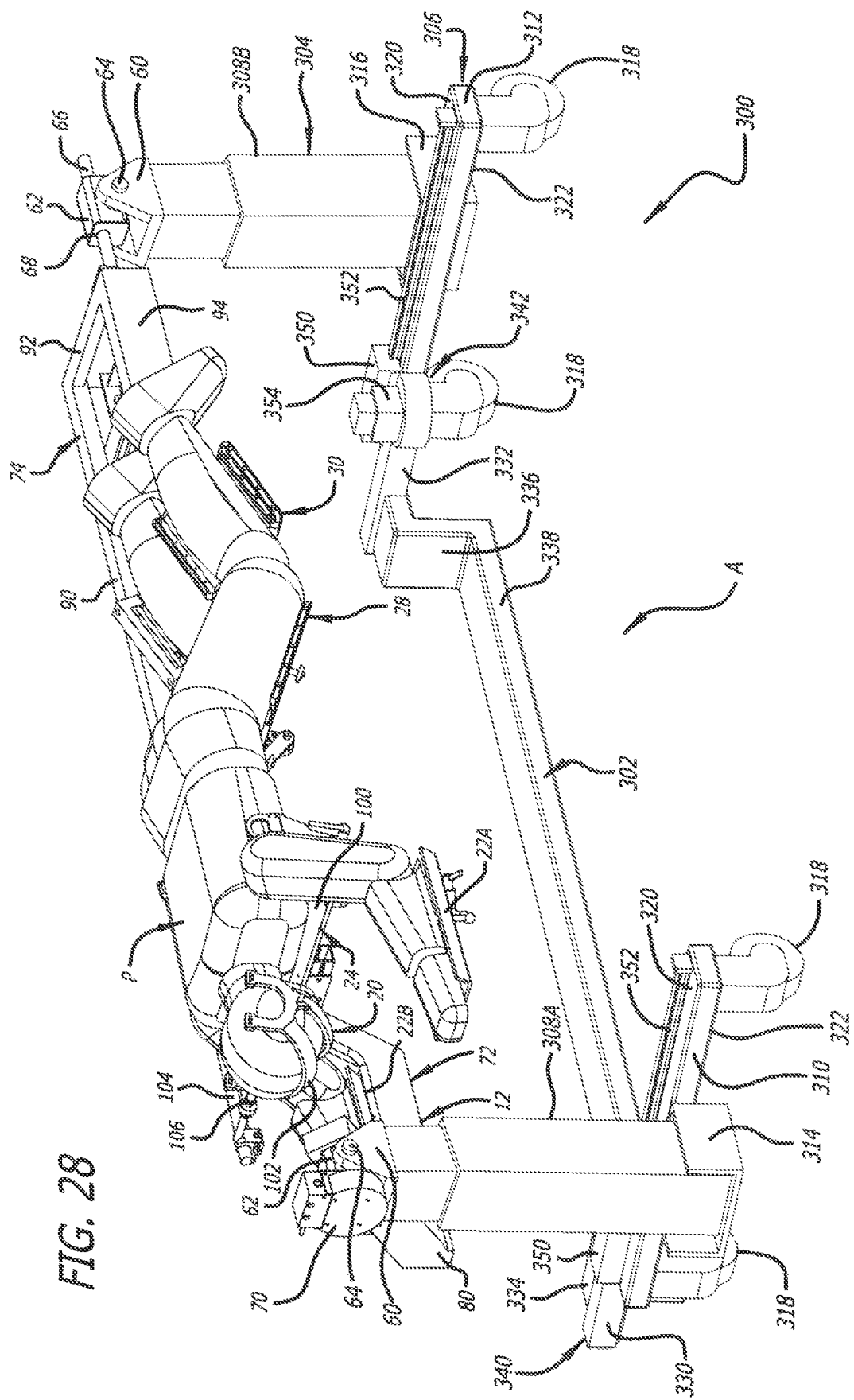
FIG. 28 is another top perspective view of the surgical frame of FIG. 27 with the patient in a prone position showing the translating beam thereof in a second position.
Figure 29:
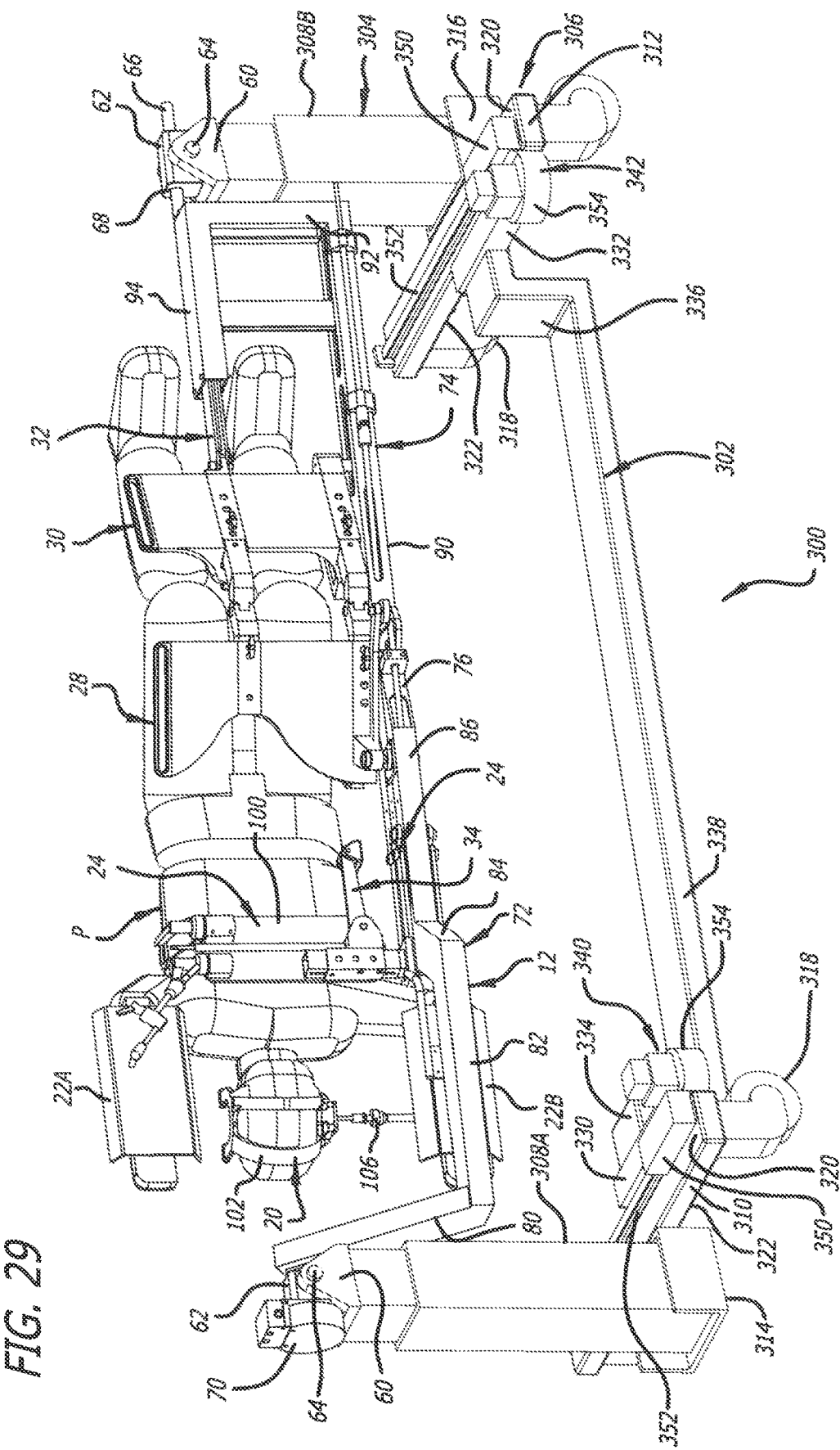
FIG. 29 is yet another top perspective view of the surgical frame of FIG. 27 with the patient in a lateral position showing the translating beam thereof in a third position.
Figure 30:
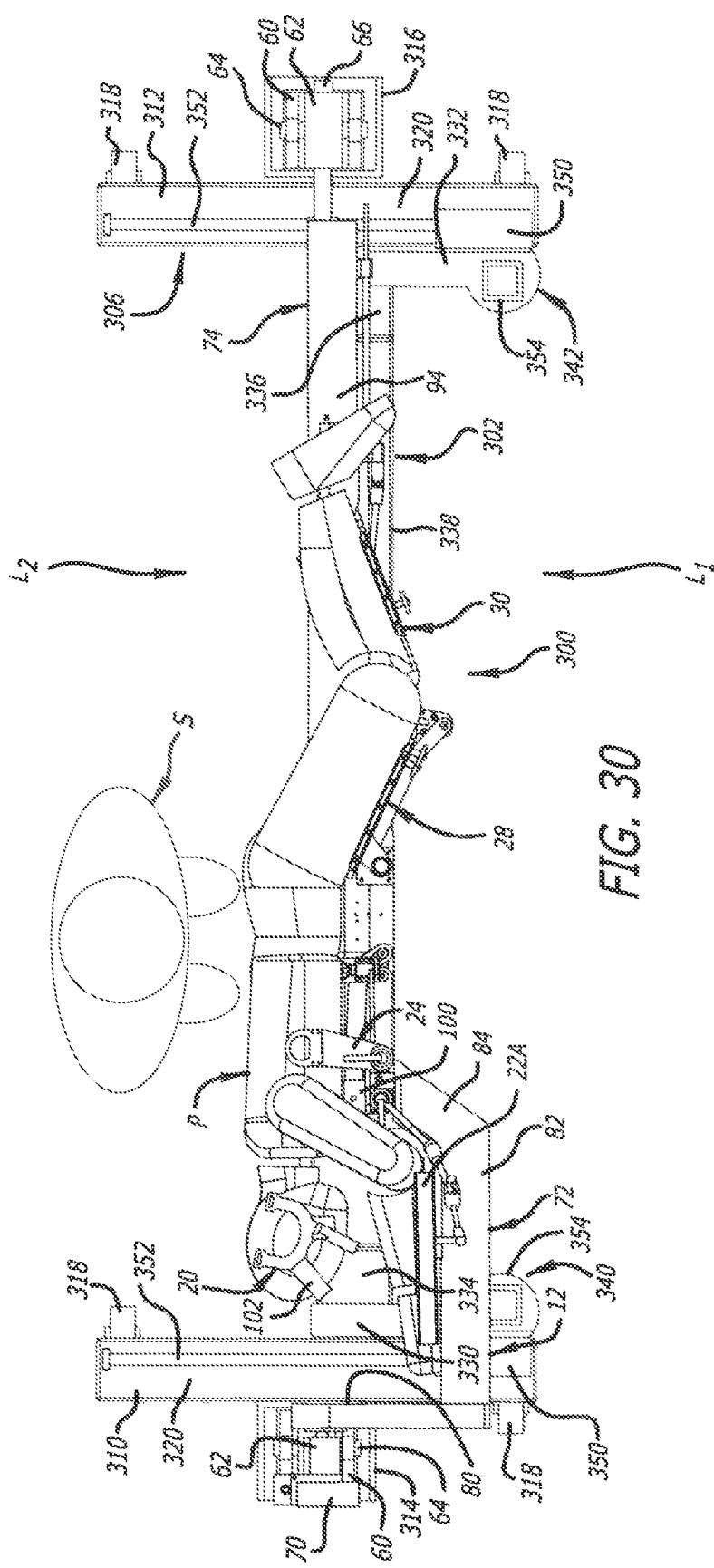
FIG. 30 is top plan view of the surgical frame of FIG. 27 with the patient in a lateral position showing the translating beam thereof in the third position.

The translating beam 302 is moveable using the first and second translation mechanisms 340 and 342 between a first terminal position (FIG. 28) and a second terminal position (FIGS. 29 and 30). The translating beam 302 is positionable at various positions (FIG. 27) between the first and second terminal positions. When the translating beam 302 is in the first terminal position, as depicted in FIG. 28, the translating beam 302 and its cross member 338 are positioned on the lateral side $L_1$ of the surgical frame 300. Furthermore, when the translating beam 302 is in the second terminal position, as depicted in FIGS. 29 and 30, the translating beam 302 and its cross member 338 are positioned in the middle of the surgical frame 300.

With the translating beam 302 and its cross member 338 moved to be positioned at the lateral side $L_1$, the surgical table/gurney and the patient P positioned thereon can be positioned under the offset main beam 12 in the patient receiving area A to facilitate transfer of the patient P to or from the offset main beam 12. As such, the position of the translating beam 302 at the lateral side $L_1$ enlarges the patient receiving area A so that the surgical table/gurney can be received therein to allow such transfer to or from the offset main beam 12.

Furthermore, with the translating beam 302 and its cross member 338 moved to be in the middle of the surgical frame 300 (FIGS. 29 and 30), a surgeon and/or a surgical assistant can have access to the patient P from either of the lateral sides $L_1$ or $L_2$. As such, the position of the translating beam 302 in the middle of the surgical frame 300 allows a surgeon and/or a surgical assistant to get close to the patient P supported by the surgical frame 300. As depicted in FIG. 30, for example, a surgeon and/or a surgical assistant can get close to the patient P from the lateral side $L_2$ without interference from the translating beam 302 and its cross member 338. The position of the translating beam 302 can be selected to accommodate access by both a surgeon and/or a surgical assistant by avoiding contact thereof with the feet and legs of a surgeon and/or a surgical assistant.

The position of the translating beam 302 and its cross member 338 can also be changed according to the rotational position of the offset main beam 12. To illustrate, the offset main beam 12 can be rotated a full 360° before, during, and even after surgery to facilitate various positions of the patient to afford various surgical pathways to the patient's spine depending on the surgery to be performed. For example, the offset main beam 12 can be positioned by the surgical frame 300 to place the patient P in a prone position (e.g., FIGS. 27 and 28), lateral positions (e.g., FIGS. 29 and 30), and in a position 45° between the prone and lateral positions. The translating beam 302 can be positioned to accommodate the rotational position of the offset main beam 12 to aid in the stability of the surgical frame 300. For example, when the patient P is in the prone position, the translating beam 302 can preferably be moved to the center of the surgical frame 300 underneath the patient P. Furthermore, when the patient P is in one of the lateral positions, the translating beam 302 can be moved toward one of the corresponding lateral sides $L_1$ and $L_2$ of the surgical frame 300 to position underneath the patient P. Such positioning of the translating beam 302 can serve to increase the stability of the surgical frame 300.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of reconfiguring a surgical frame before, during, or after surgery, the method comprising:

providing the surgical frame including a support platform, a first support portion, a second support portion, and a main beam spaced from the ground by the support platform, the first support portion, and the second support portion, the support platform including a translating beam moveable between a first position at or adjacent a first lateral side of the surgical frame and a second position at or adjacent a second lateral side of the surgical frame, the main beam being configured to receive a patient thereon, the main beam and the patient received thereon being rotatable relative to the support platform, the first support portion, and the second support portion;

supporting the patient by the main beam of the surgical frame;

rotating the patient to a prone position, and moving the translating beam to a position underneath the patient supported in the prone position; and rotating the patient to one of a first lateral position and a second lateral position, and moving the translating beam to a position underneath the patient supported in the one of the first lateral position and the second lateral position.

2. The method of claim 1, further comprising:

moving the translating beam to one of the first lateral side and the second lateral side of the surgical frame;

positioning a surgical table/gurney with the patient laying thereon under the main beam in a patient receiving area, the patient receiving area being defined in part by the translating beam; and transferring the patient from the surgical table/gurney to the main beam from the surgical table/gurney.

3. The method of claim 2, further comprising:

removing the surgical table/gurney from the patient receiving area; and moving the translating beam away from the one of the first lateral side and the second lateral side of the surgical frame.

4. The method of claim 1, further comprising:

moving the translating beam to a position to avoid contact with feet and/or legs of a surgeon operating on the patient.

5. The method of claim 1, further comprising:

automatically positioning the translating beam underneath the patient as the patient is rotated with the main beam.

6. The method of claim 1, wherein the translating beam joins portions of the surgical frame together between the first and second support portions.

7. The method of claim 1, wherein the first support portion includes a first support post, and the second support portion includes a second support post, the first and second support posts each being moveable between an upper height position and a lower height position to facilitate increasing and decreasing heights thereof.

8. The method of claim 7, further comprising:

raising the first and second support posts to the upper heights thereof;

moving the translating beam to one of the first lateral side and the second lateral side of the surgical frame;

positioning a surgical table/gurney with the patient laying thereon under the main beam in a patient receiving area, the patient receiving area being defined in part by the translating beam;

lowering the first and second support posts to position the main beam adjacent the patient laying on the surgical table/gurney; and transferring the patient from the surgical table/gurney to the main beam from the surgical table/gurney.

9. A method of reconfiguring a surgical frame before, during, or after surgery, the method comprising:

spacing a main beam of the surgical frame from the ground with a first support portion and a second support portion;

supporting a patient by the main beam of the surgical frame;

rotating the main beam and the patient positioned thereon from a prone position to one of a first lateral position and a second lateral position; and moving a translating beam under the main beam and the patient positioned thereon, the translating beam being moveable between a first position at or adjacent a first lateral side of the surgical frame and a second position at or adjacent a second lateral side of the surgical frame, and the translating beam joining portions of the surgical frame together between the first and second support portions.

10. The method of claim 9, further comprising:

moving the translating beam to one of the first lateral side and the second lateral side of the surgical frame;

positioning a surgical table/gurney with the patient laying thereon under the main beam in a patient receiving area, the patient receiving area being defined in part by the translating beam; and transferring the patient from the surgical table/gurney to the main beam from the surgical table/gurney.

11. The method of claim 10, further comprising:

removing the surgical table/gurney from the patient receiving area; and moving the translating beam away from the one of the first lateral side and the second lateral side of the surgical frame.

12. The method of claim 9, further comprising:

automatically positioning the translating beam underneath the patient as the patient is rotated with the main beam.

13. The method of claim 9, wherein the first support portion includes a first support post, and the second support portion includes a second support post, the first and second support posts each being moveable between an upper height position and a lower height position to facilitate increasing and decreasing heights thereof.

14. The method of claim 13, further comprising:

raising the first and second support posts to the upper heights thereof;

moving the translating beam to one of the first lateral side and the second lateral side of the surgical frame;

positioning a surgical table/gurney with the patient laying thereon under the main beam in a patient receiving area, the patient receiving area being defined in part by the translating beam;

lowering the first and second support posts to position the main beam adjacent the patient laying on the surgical table/gurney; and transferring the patient from the surgical table/gurney to the main beam from the surgical table/gurney.

15. A method of reconfiguring a surgical frame before, during, or after surgery, the method comprising:

spacing a main beam of the surgical frame and a patient positioned on the main beam from the ground with a first support portion and a second support portion;

rotating the main beam and the patient positioned thereon from a prone position to one of a first lateral position and a second lateral position; and moving a translating beam under the main beam and the patient positioned thereon, the translating beam being moveable between a first position at or adjacent a first lateral side of the surgical frame and a second position at or adjacent a second lateral side of the surgical frame, and the translating beam joining portions of the surgical frame together between the first and second support portions.

16. The method of claim 15, further comprising:
moving the translating beam to one of the first lateral side and the second lateral side of the surgical frame;
positioning a surgical table/gurney with the patient laying thereon under the main beam in a patient receiving area, the patient receiving area being defined in part by the translating beam; and
transferring the patient from the surgical table/gurney to the main beam from the surgical table/gurney.

17. The method of claim 16, further comprising:
removing the surgical table/gurney from the patient receiving area; and
moving the translating beam away from the one of the first lateral side and the second lateral side of the surgical frame.

18. The method of claim 15, further comprising:
automatically positioning the translating beam underneath the patient as the patient is rotated with the main beam.

19. The method of claim 15, wherein the first support portion includes a first support post, and the second support portion includes a second support post, the first and second support posts each being moveable between an upper height position and a lower height position to facilitate increasing and decreasing heights thereof.

20. The method of claim 19, further comprising:
raising the first and second support posts to the upper heights thereof;
moving the translating beam to one of the first lateral side and the second lateral side of the surgical frame;
positioning a surgical table/gurney with the patient laying thereon under the main beam in a patient receiving area, the patient receiving area being defined in part by the translating beam;
lowering the first and second support posts to position the main beam adjacent the patient laying on the surgical table/gurney; and
transferring the patient from the surgical table/gurney to the main beam from the surgical table/gurney.

* * * * *